(12) United States Patent
Tiainen et al.

(10) Patent No.: US 9,889,011 B2
(45) Date of Patent: Feb. 13, 2018

(54) HARD SCAFFOLD

(71) Applicant: CORTICALIS AS, Rud (NO)

(72) Inventors: Hanna Tiainen, Oslo (NO); Havard J. Haugen, Oslo (NO); S. Petter Lyngstadaas, Nesoddtangen (NO)

(73) Assignee: CORTICALIS AS, Rud (NO)

( * ) Notice: Subject to any disclaimer, the term of this patent is extended or adjusted under 35 U.S.C. 154(b) by 265 days.

(21) Appl. No.: 14/427,901

(22) PCT Filed: Sep. 17, 2013

(86) PCT No.: PCT/EP2013/069250
§ 371 (c)(1),
(2) Date: Mar. 12, 2015

(87) PCT Pub. No.: WO2014/044666
PCT Pub. Date: Mar. 27, 2014

(65) Prior Publication Data
US 2015/0223938 A1    Aug. 13, 2015

(30) Foreign Application Priority Data

Sep. 18, 2012 (SE) ...................................... 1251044

(51) Int. Cl.
*A61F 2/28* (2006.01)
*A61L 27/06* (2006.01)
*A61L 27/10* (2006.01)
*A61L 27/30* (2006.01)
*A61L 27/56* (2006.01)

(52) U.S. Cl.
CPC ................ *A61F 2/28* (2013.01); *A61L 27/06* (2013.01); *A61L 27/10* (2013.01); *A61L 27/306* (2013.01); *A61L 27/56* (2013.01); *A61F 2210/0076* (2013.01); *A61F 2240/001* (2013.01); *A61F 2310/00227* (2013.01); *A61L 2430/12* (2013.01)

(58) Field of Classification Search
CPC ........ A61L 27/306; A61L 27/10; A61L 27/02; A61F 240/00227; A61F 2/28
USPC ........................................................ 427/294
See application file for complete search history.

(56) References Cited

PUBLICATIONS

Tiainen et al. Ultra porous titanium oxide scaffold with high compressive strength. J. Materials Science: Materials Medicine (2010) vol. 21 pp. 2783-2792.*
Vogt et al. Improving the properties of ceramic foams by a vacuum infiltration process. Journal of the European Ceramic Society. vol. 30. Issue Nov. 14, 2010 pp. 3005-3011.*
Fostad et al. Loadable TiO2 scaffolds—A correlation study between processing parameters, micro CT analysis and mechanical strength. Journal of the European Ceramic Society. vol. 29. Issue 13. Oct. 2009. pp. 2773-2781.*

* cited by examiner

*Primary Examiner* — Cachet I Sellman
(74) *Attorney, Agent, or Firm* — Cermak Nakajima & McGowan LLP; Malcolm K. McGowan

(57) ABSTRACT

The present document is directed to medical implants in the form of titanium dioxide scaffolds. Disclosed is a method for producing titanium dioxide scaffolds having an increased mechanical strength by recoating the titanium dioxide scaffold with a low viscosity titanium dioxide slurry in a vacuum infiltration process followed by sintering of the scaffold. The document is also directed to the recoated titanium dioxide scaffolds produced and their uses as medical implants.

15 Claims, 9 Drawing Sheets

HARD SCAFFOLD

CROSS-REFERENCE TO RELATED APPLICATION

This application is a National Stage Application under 35 U.S.C. § 371 and claims the benefit of International Application No. PCT/EP2013/069250, filed Sep. 17, 2013, which claims priority to Swedish Application No. 1251044-2, filed on Sep. 18, 2012. The disclosures of the foregoing applications are hereby incorporated by reference in their entirety.

TECHNICAL FIELD

The present document is direct to scaffold structures which may be used in medical applications as medical prosthetic devices. The document discloses a method for producing titanium dioxide scaffolds having an improved mechanical strength by a recoating procedure and scaffolds produced by this method. The scaffolds have a high mechanical strength while the necessary pore architecture is left basically unaffected by the method for improving the strength.

BACKGROUND OF THE INVENTION

Conditions such as trauma, tumours, cancer, periodontitis and osteoporosis may lead to bone loss, reduced bone growth and volume. For these and other reasons it is of great importance to find methods to improve bone growth and to regain bone anatomy. Scaffolds may be used as a framework for the cells participating in the bone regeneration process, but also as a framework as a substitute for the lost bone structure. It is also of interest to provide a scaffold to be implanted into a subject having a surface structure that stimulates the bone cells to grow allowing a coating of the implanted structure by bone after a healing process.

Orthopaedic implants are utilized for the preservation and restoration of the function in the musculoskeletal system, particularly joints and bones, including alleviation of pain in these structures. Orthopaedic implants are commonly constructed from materials that are stable in biological environments and that withstand physical stress with minimal deformation. These materials must possess strength, resistance to corrosion, have a good biocompatibility and have good wear properties. Materials which fulfil these requirements include biocompatible materials such as titanium and cobalt-chrome alloy.

For the purposes of tissue engineering it is previously known to use scaffolds to support growth of cells. It is believed that the scaffold pore size (pore diameter), porosity and interconnectivity are important factors that influence the behaviour of the cells and the quality of the tissue regenerated. Prior art scaffolds are typically made of calcium phosphates, hydroxyl apatites and of different kinds of polymers.

One principle of tissue engineering is to harvest cells, expand the cell population in vitro, if necessary, and seed them onto a supporting three-dimensional scaffold, where the cells can grow into a complete tissue or organ. For most clinical applications, the choice of scaffold material and structure is crucial. In order to achieve a high cell density within the scaffold, the material needs to have a high surface area to volume ratio. The pores must be open and large enough such that the cells can migrate into the scaffolds. When cells have attached to the material surface there must be enough space and channels to allow for nutrient delivery, waste removal, exclusion of material or cells and protein transport, which is only obtainable with an interconnected network of pores. Biological responses to implanted scaffolds are also influenced by scaffold design factors such as three-dimensional microarchitecture. In addition to the structural properties of the material, physical properties of the material surface for cell attachment are essential.

Bone in-growth is known to preferentially occur in highly porous, open cell structures in which the cell size is roughly the same as that of trabecular bone (approximately 0.25-0.5 mm), with struts roughly 100 µm (0.1 mm) in diameter. Materials with high porosity and possessing a controlled microstructure are thus of interest to both orthopaedic and dental implant manufacturers. For the orthopaedic market, bone in-growth and on-growth options currently include the following: (a) DePuy Inc. sinters metal beads to implant surfaces, leading to a microstructure that is controlled and of a suitable pore diameter for bone in-growth, but with a lower than optimum porosity for bone in-growth; (b) Zimmer Inc. uses fibre metal pads produced by diffusion bonding loose fibers, wherein the pads are then diffusion bonded to implants or insert injection moulded in composite structures, which also have lower than optimum density for bone in-growth; (c) Biomet Inc. uses a plasma sprayed surface that results in a roughened surface that produces on-growth, but does not produce bone in-growth; and (d) Implex Corporation produces using a chemical vapor deposition process to produce a tantalum-coated carbon microstructure that has also been called a metal foam. Research has suggested that this "trabecular metal" leads to high quality bone in-growth. Trabecular metal has the advantages of high porosity, an open-cell structure and a cell size that is conducive to bone in-growth. However, trabecular metal has a chemistry and coating thickness that are difficult to control. Trabecular metal is very expensive, due to material and process costs and long processing times, primarily associated with chemical vapour deposition (CVD).

Furthermore, CVD requires the use of very toxic chemicals, which is disfavoured in manufacturing and for biomedical applications.

In order to ensure viable cell attachment, nutrient and waste product transportation, vascularisation, and passage of the newly formed bone tissue throughout the entire scaffold volume, a bone scaffold is required to have a well-interconnected pore network with large pore volume and an average pore connection size preferably exceeding 100 µm. In addition to the reticulated pore space, appropriate pore morphology and average pore diameter larger than 300 µm are necessary to provide adequate space and permeability for viable bone formation in a non-resorbable scaffold structure. However, one of the most important prerequisites for the scaffold structure is that the scaffold material itself is fully biocompatible and favours bone cell attachment and differentiation on its surface to promote the formation of a direct bone-to-scaffold interface.

Ceramic $TiO_2$ has been identified as a promising material for scaffold-based bone tissue repair, and highly porous $TiO_2$ scaffolds have previously been shown to provide a favourable microenvironment for viable bone ingrowth from surrounding bone tissue in vivo. The excellent osteoconductive capacity of these $TiO_2$ scaffolds has been attributed to the large and highly interconnected pore volume of the $TiO_2$ foam structure. However, as the mechanical properties of a scaffold are governed not only by the scaffold material but also by the pore architecture of the scaffold structure, increasing pore diameters and porosity are known to have a detrimental effect on the mechanical properties of cellular solids, and consequently reduce the structural integrity of the scaffold construct. As one of the key features of a bone scaffolds is to provide mechanical support to the defect site during the regeneration of bone tissue, the lack of sufficient mechanical strength limits the use of the $TiO_2$ scaffold structure to skeletal sites bearing only moderate physiological loading. The mechanical properties of such ceramic $TiO_2$ foams should therefore be improved through optimized processing so as to produce bone scaffolds with adequate load-bearing capacity for orthopaedic applications without compromising the desired pore architectural features of the highly porous $TiO_2$ bone scaffolds.

Reticulated ceramic foams, such as those of WO08078164, have recently attracted increasing interest as porous scaffolds that stimulate and guide the natural bone regeneration in the repair of non-healing, or critical size, bone defects. Since the purpose of such a bone scaffold is to provide optimal conditions for tissue regeneration, the foam structure must allow bone cell attachment onto its surface as well as provide sufficient space for cell proliferation and unobstructed tissue ingrowth. Therefore, structural properties, such as porosity and pore morphology, of the 3D bone scaffold construct play a crucial role in the success of scaffold-based bone regeneration. Reticulated ceramic foams may be produced by a so called replication method or the polymer sponge method. This method was first described by Somers and Schwartzwalder in 1963. In short, such a method comprises coating a porous, combustible structure with a metal oxide slurry, and removing the porous structure by heating at high temperatures, which causes the removal of the porous structure and fusion of the metal oxide particles.

The mechanical properties of reticulated ceramic foams prepared by replication method are strongly dependent on the size and distribution of cracks and flaws in the foam structure, which typically determine the strength of the foam struts (Brezny et al. 1989). However, it has been an object in may studies to try to enhance the mechanical strength by optimising the various processing steps involved in the replication process.

Vogt et al. 2010 have previously described a vacuum infiltration process in which the hollow interior the replicated foams struts is filled with ceramic slurry, thus resulting in an increase in the compressive strength of these ceramic foams. However, the hollow space inside the ceramic struts can be considered practically closed porosity and the infiltration of the ceramic slurry into this hollow space is likely to be limited even under vacuum, particularly in foams with smaller strut sizes with narrower triangular voids within the strut interior. Thus, it may be speculated that the improved mechanical strength obtained by the method of Vogt et al 2010 mainly depends on a an effect of strengthening the outer surface parts of the scaffold without a concomitant strengthening of the more inner parts of the scaffold. Also, the method of Vogt et al. 2010 is expected to affect the pore architecture by making the pores narrower.

As is evident from the above, there still exists a need in the field of medical prosthetic devices for scaffold structures having high mechanical strength and a well formed pore network. The object of the present document is to overcome or at least mitigate some of the problems associated with the prior art.

SUMMARY OF INVENTION

The present document is directed to a titanium dioxide ($TiO_2$) scaffold having a mechanical strength making it suitable for use as a medical prosthetic device. It is therefore an object of the present disclosure to provide a titanium dioxide scaffold to be used as a medical prosthetic device for implantation into a subject that e.g. has a good biocompatibility and does not cause adverse reactions when implanted into a subject, which allows for cell growth into the 3-dimensional scaffold and which still has a mechanical stability which allows it to be practically useful as a stabilizing structure.

In one aspect, this document is directed to a method for producing a recoated titanium dioxide scaffold, said method comprising:
  a) applying a first slurry comprising titanium dioxide to a combustible porous structure
  b) allowing the first slurry to solidify on said combustible porous structure;
  c) removing said combustible porous structure from the solidified titanium dioxide slurry by a first sintering at about 400-550° C. to produce a titanium dioxide scaffold structure;
  d) subjecting the titanium dioxide scaffold structure of step c) to a second sintering at a temperature of at least 1300° C. for at least 10 hours to provide a single-coated titanium dioxide scaffold
    characterized in that said method further comprises a vacuum infiltration procedure, wherein said vacuum infiltration procedure comprises the steps of
  e) applying a second slurry comprising titanium dioxide to said single coated titanium dioxide scaffold by vacuum infiltration and thereafter optionally subjecting said single-coated titanium dioxide scaffold to centrifugation;
  f) allowing the second slurry of step e) to solidify on the single-coated titanium dioxide scaffold; and
  g) performing a third sintering at a temperature of at least 1100° C. to provide a recoated titanium dioxide scaffold.

The vacuum-infiltration procedure of steps e)-g) in the above method may also be preceded or followed by a double-coating procedure comprising the steps of:
  i) applying a third slurry comprising titanium dioxide to the single-coated titanium dioxide scaffold of step d) or the recoated titanium dioxide scaffold of step g) and optionally subjecting the scaffold to centrifugation;
  ii) allowing the third slurry of step i) to solidify on the scaffold; and
  iii) performing a further sintering at a temperature of at least 1100° C.

The method for producing a recoated titanium dioxide scaffold may therefore comprise or consist of the following steps, presented in the order they are performed in the respective alternative:
  1. Steps a)-g)
  2. Steps a)-d), steps i)-iii), steps e)-g)
  3. Steps a)-g), steps i)-iii)

By performing the method according to alternatives 1, 2 or 3 above, a recoated titanium dioxide scaffold is produced. Titanium dioxide scaffolds produced by the method according to alternatives 1, 2 or 3 are in the present context collectively denoted recoated titanium dioxide scaffolds. The present document is also directed to a recoated titanium dioxide scaffold obtained or obtainable by performing a method according to alternatives 1, 2 or 3 above.

This document is therefore also directed to a recoated titanium dioxide scaffold obtainable by the method of
  a) applying a first slurry comprising titanium dioxide to a combustible porous structure b) allowing the slurry to solidify on said combustible porous structure;
c) removing said combustible porous structure from the solidified titanium dioxide slurry by a first sintering at about 400-550° C. to produce a titanium dioxide scaffold structure;
d) subjecting the titanium dioxide scaffold structure of step c) to a second sintering at a temperature of at least 1300° C. for at least 10 hours to provide a single-coated titanium dioxide scaffold
characterized in that said method further comprises a vacuum infiltration procedure, wherein said vacuum infiltration procedure comprises the steps of
e) applying a second slurry comprising titanium dioxide to said single coated titanium dioxide scaffold by vacuum infiltration and thereafter optionally subjecting said single-coated titanium dioxide scaffold to centrifugation;
f) allowing the second slurry of step e) to solidify on the single-coated titanium dioxide scaffold; and
g) performing a third sintering at a temperature of at least 1100° C. to provide a recoated titanium dioxide scaffold,
wherein the vacuum infiltration procedure of steps e)-g) is optionally preceded or followed by a double-coating procedure comprising the steps of:
i) applying a third slurry comprising titanium dioxide to the single-coated titanium dioxide scaffold of step d) or the recoated titanium dioxide scaffold of step g) and optionally subjecting the scaffold to centrifugation;
ii) allowing the third slurry of step i) to solidify on the scaffold; and
iii) performing a further sintering at a temperature of at least 1100° C.

This document also discloses a medical prosthetic device comprising a recoated titanium dioxide scaffold obtainable by the above method. The document is also directed to this recoated titanium dioxide scaffold for use a medical prosthetic device.

Further, this document is directed to a method for the regeneration, repair, substitution and/or restoration of tissue comprising the implantation into a subject in need thereof of a recoated titanium dioxide scaffold as disclosed herein or a medical prosthetic device comprising it and the use of a recoated titanium dioxide scaffold or a medical prosthetic device comprising it for the regeneration, repair, substitution and/or restoration of tissue. Also disclosed is a recoated titanium dioxide scaffold or a medical prosthetic device comprising it for use for the regeneration, repair, substitution and/or restoration of tissue and the use of a recoated titanium dioxide scaffold for the preparation of a medical prosthetic device for the regeneration, repair, substitution and/or restoration of tissue.

Since the recoated titanium dioxide scaffold of this document is made of titanium dioxide which has a good biocompatibility, the risk for adverse reactions, such as allergic reactions, is reduced when the scaffolds are implanted into a subject. The recoated titanium dioxide scaffolds also have a beneficial effect on the regeneration of tissue due to the material they are made of and their surface structure. Due to the use of vacuum infiltration in the recoating procedure, the recoated titanium dioxide scaffolds in addition have a stability which is particularly suitable for their use in medical implants having enough stability to provide a stabilizing function while still not being too rigid.

Other features and advantages of the invention will be apparent from the following detailed description, drawings, examples, and from the claims.

DEFINITIONS

"Scaffold" in the present context relates to an open porous structure. By "titanium dioxide scaffold" is meant a scaffold comprising predominantly titanium dioxide as the building material for the scaffold structure (i.e. more than 50 wt % titanium dioxide, such as about at least 51 wt %, 60 wt %, 70 wt %, 80 wt %, 90 wt %, 95 wt %, 96 wt %, 97 wt %, 98 wt %, 99 wt % or 100 wt % titanium dioxide, such as about 51-100 wt %, 60-100 wt %, 60-90 wt %, 70-100 wt %, 70-90 wt %, 80-90 wt %, or 80-95 wt % titanium dioxide). The titanium dioxide scaffold may thus comprise or consist of titanium dioxide as the building material for the scaffold. The scaffold may in addition comprise other substances, such as a surface coating of biologically active molecules.

By "pore diameter" is in the context of the present document intended the hydraulic diameter of a pore without its surrounding walls. The hydraulic diameter is well known to the person skilled in the art and is defined as 4*area of a pore divided by the circumferential length of the pore.

"Fractal dimension strut" is a statistical quantity that gives an indication of how completely a fractal appears to fill space, as one zooms down to finer and finer scales. There are many specific definitions of fractal dimension and none of them should be treated as the universal one. A value of 1 pertains to a straight line. The higher the number the more complex is the surface structure. Fractal dimension is in the present document calculated using the Kolmogorov or "box counting" method (Larry S. et al. 1989). It is calculated in both 2 d and 3 d in Skyscan CTAn, Kontich, Belgium. The surface or volume is divided into an array of equal squares or cubes, and the number of squares containing part of the object surface is counted. This is repeated over a range of box sizes such as 3-100 pixels. The number of boxes containing surface is plotted against box length in a log-log plot, and the fractal dimension is obtained from the slope of the log-log regression.

"Total porosity" or "porosity" is in the present context defined as all compartments within a body which is not a material, i.e. the space not occupied by any material. Total porosity involves both closed and open pores.

By "inner strut volume" is meant the volume of the inner lumen of the strut.

"Vacuum infiltration" in the present context refers to a process for forcing liquid into an object by a pressure of 100 kPa or less.

By "sintering", "sinter" and the like is meant a method for making objects from powder by heating the material (below its melting point) until its particles adhere to each other (fuse). Sintering is traditionally used for manufacturing ceramic objects, and has also found uses in fields such as powder metallurgy.

By "reticulated foam" is in the present context intended a porous and open solid foam. By "reticulated ceramic foam" is intended an open porous structure made up of a ceramic material, such as titanium dioxide. A reticulated ceramic foam may be produced by a replication method comprising the steps of coating a porous, combustible structure with a metal oxide slurry, and removing the porous, combustible structure by heating at high temperatures, which causes the removal of the porous, combustible structure and fusion of the metal oxide particles, thus forming a ceramic porous structure.

A "medical prosthetic device", "medical implant", "implant" and the like in the present context relates to a device intended to be implanted into the body of a vertebrate animal, such as a mammal, e.g. a human mammal. Implants in the present context may be used to replace anatomy and/or restore any function of the body. Examples of such devices include, but are not limited to, dental implants and orthopaedic implants. In the present context, orthopaedic implants includes within its scope any device intended to be implanted into the body of a vertebrate animal, in particular a mammal such as a human, for preservation and restoration of the function of the musculoskeletal system, particularly joints and bones, including the alleviation of pain in these structures. In the present context, dental implant includes within its scope any device intended to be implanted into the oral cavity of a vertebrate animal, in particular a mammal such as a human, in tooth restoration procedures. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation may alone be referred to as an implant even if other parts are to be connected thereto. Orthopaedic and dental implants may also be denoted as orthopaedic and dental prosthetic devices as is clear from the above.

In the present context, "subject" relates to any vertebrate animal, such as a bird, reptile, mammal, primate and human.

By "ceramics" are in the present context meant objects of inorganic powder material treated with heat to form a solidified structure.

By "soft tissue" is in the context of the present document intended tissues that connect, support, or surround other structures and organs of the body, not being bone. Soft tissue includes ligaments, tendons, fascia, skin, fibrous tissues, fat, synovial membranes, epithelium, muscles, nerves and blood vessels.

By "hard tissue" is in the context of the present document intended mineralized tissues, such as bone and teeth, and cartilage. Mineralized tissues are biological tissues that incorporate minerals into soft matrices.

DETAILED DESCRIPTION OF THE INVENTION

Figure 1A:
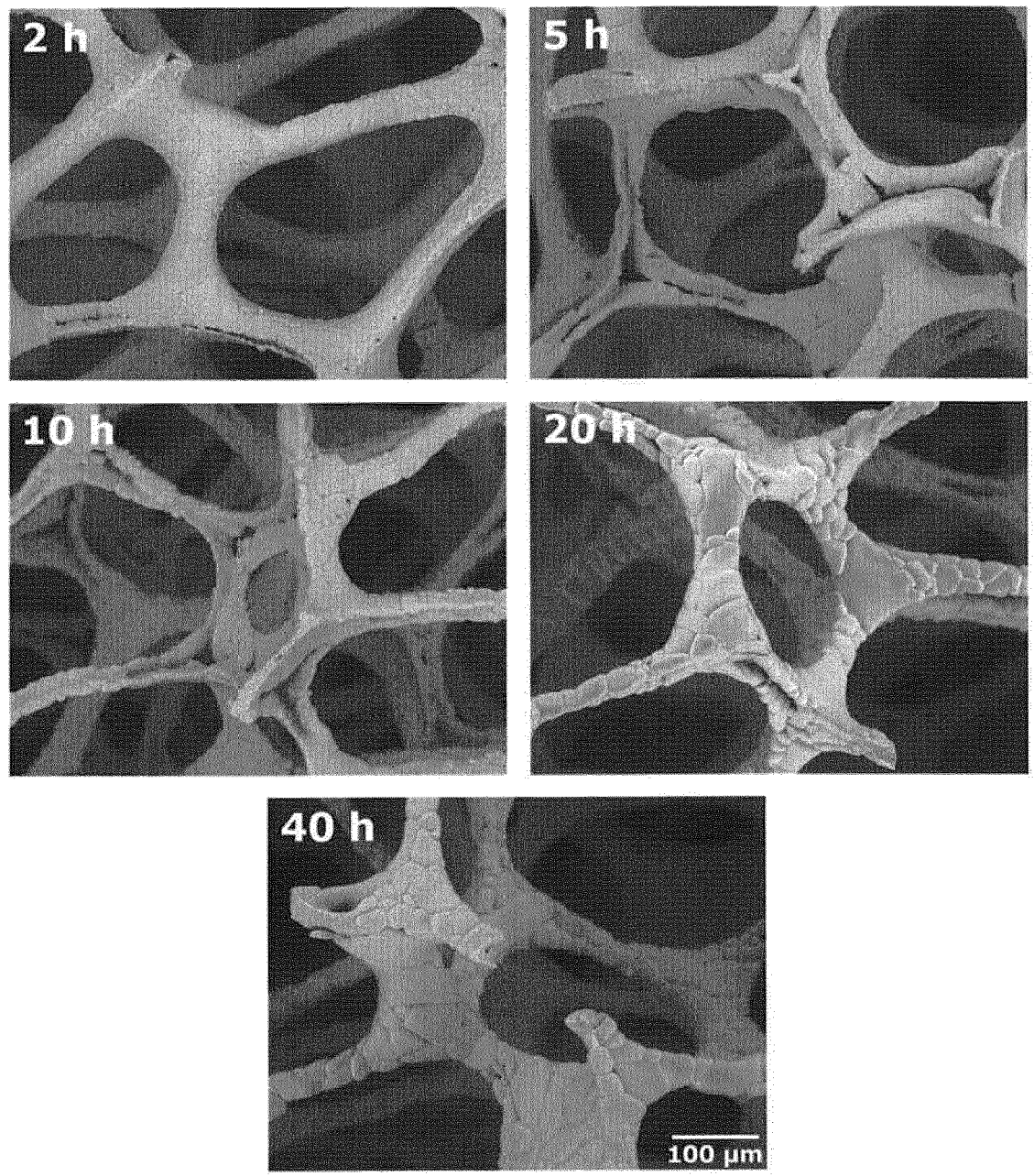
FIG. 1 shows the effect of sintering time at 1500° C. on the microscopic appearance of the $TiO_2$ scaffolds (FIG. 1a) and their compressive strength (FIG. 1b). Statistically significant difference in comparison to foams sintered for 2 h (*,**) and 10 h (#,##). *$p<0.05$ and **,##$p<0.01$, n=10.

The present document relates to recoated titanium dioxide scaffolds having a high biocompatibility and a mechanical stability which makes them useful in medical implants. The document also relates to methods for producing such recoated titanium dioxide scaffolds and uses thereof.

The titanium dioxide scaffold of the present document is a reticulated scaffold which may function as a structural support which allows tissue formation by creating a three dimensional space for cellular attachment and ingrowth. The titanium dioxide of the scaffold provides a scaffold which is biocompatible and which can be processed into different shapes to provide mechanical support and a framework for cellular growth. Thus, the titanium dioxide scaffold provides a suitable structure to be used in tissue engineering, such as for regeneration of bone.

Flaws and irregularities in the strut structure are known have a strong influence on the mechanical properties of reticulated ceramic foams, and the strut strength may therefore be optimised by improving the processing method. In the present document, process parameters were optimized to improve the mechanical properties of titanium dioxide scaffolds. It was demonstrated that long sintering times at high temperatures led to an inward collapse of one of the walls of the triangular voids typically found in the strut interior of foams prepared using the replication method. This strut folding led to increased compressive strength, while the pore architectural features were not significantly affected.

Furthermore, the majority of the internal porosity of the foam struts was partially eliminated and became accessible for infiltration with $TiO_2$ slurry. The recoating procedure disclosed herein was found to markedly reduce the flaw size and number in the $TiO_2$ foam struts, which led to significant strengthening of the ceramic structure by improved structural uniformity and slightly increased strut diameter.

In one aspect, this document is therefore directed to a method for producing a recoated titanium dioxide scaffold, said method comprising:
  a) applying a first slurry comprising titanium dioxide to a combustible porous structure;
  b) allowing the first slurry to solidify on said combustible porous structure;
  c) removing said combustible porous structure from the solidified titanium dioxide slurry by a first sintering at about 400-550° C. to produce a titanium dioxide scaffold structure;
  d) subjecting the titanium dioxide scaffold structure of step c) to a second sintering at a temperature of at least 1300° C. for at least 10 hours to provide a single-coated titanium dioxide scaffold;

characterized in that said method further comprises a vacuum infiltration procedure, wherein said vacuum infiltration procedure comprises the steps of e) applying a second slurry comprising titanium dioxide to said single coated titanium dioxide scaffold by vacuum infiltration and thereafter optionally subjecting said single-coated titanium dioxide scaffold to centrifugation;

f) allowing the second slurry of step e) to solidify on the single-coated titanium dioxide scaffold; and g) performing a third sintering at a temperature of at least 1100° C. to provide a recoated titanium dioxide scaffold.

The vacuum infiltration procedure of steps e)-g) may also be preceded or followed by a double coating procedure comprising the steps of i) applying a third slurry comprising titanium dioxide to the single-coated titanium dioxide scaffold of step d) or the recoated titanium dioxide scaffold of step g) and optionally subjecting the scaffold to centrifugation;

ii) allowing the third slurry of step i) to solidify on the scaffold; and iii) performing a further sintering at a temperature of at least 1100° C.

The structure resulting by performing steps a)-c) in the above method may in the present document be referred to as a titanium dioxide scaffold structure. The scaffolds produced after steps a)-d) may in the present document be referred to as "single-coated" (SC) scaffolds or sintered titanium dioxide scaffolds. Steps i)-iii) are in the present context referred to as a double coating (DC) and result in a double-coated (DC) scaffold when preceded by at least steps a)-d). The process of steps e)-g) is in the present referred to as a vacuum infiltration (VI) process. A scaffold subjected to steps e)-g) may therefore be denoted a vacuum infiltrated (VI) scaffold. By performing step a)-d) and then steps e)-g), a SC+VI scaffold or recoated titanium dioxide scaffold is produced. By performing steps a)-d), then steps e)-g) before steps i)-iii), a VI+DC scaffold or recoated titanium dioxide scaffold is produced. By performing steps a)-d) before steps i)-iii) and then performing steps e)-g), a DC+VI scaffold or recoated titanium dioxide scaffold is produced. The above abbreviations denoting different kinds of scaffolds and how they are produced may be referred to in other parts of this document. However, the term "recoated titanium dioxide scaffold(s)" or "recoated scaffold(s)", as used in this document, collectively refers to titanium dioxide scaffolds which have been produced by performing steps a)-d) directly followed by steps e)-g), titanium dioxide scaffolds which have been produced by performing steps i)-iii) after steps a)-d) but before steps e)-g) and titanium dioxide scaffolds produced by performing steps a)-g) before steps i)-iii). The present document is therefore also directed to a recoated titanium dioxide scaffold obtainable by or obtained by performing steps a)-d) directly followed by steps e)-g), a recoated titanium dioxide scaffold wherein steps i)-iii) have been performed after steps a)-d) but before steps e)-g) and a recoated titanium dioxide scaffold wherein steps a)-g) have been performed before steps i)-iii).

It was surprisingly found that the order of the double coating (steps i)-iii)) and vacuum infiltration (steps e)-g)), resulting in DC+VI or VI+DC scaffolds did not cause any significant alterations in either the pore architectural characteristics or the compressive strength of the resulting recoated scaffolds.

The first stage of the method for producing a recoated titanium dioxide scaffold involves the provision of a titanium dioxide scaffold. This may be provided e.g. by the performing method steps a)-d) or by performing the methods disclosed in WO 08/078164, such as by the hot plate moulding process or polymer sponge method (also denoted polymer sponge replication method) disclosed therein. Even though preferred, it is therefore not necessary to provide the titanium dioxide scaffold to be subjected to DC (steps i)-iii)) and/or VI (steps e)-g)) by the method of steps a)-d) but other methods also providing a titanium dioxide scaffold may be used. The present document is therefore also directed to a method for increasing the mechanical strength of a titanium dioxide scaffold, which method comprises providing a titanium dioxide scaffold (such as the single-coated scaffold provided by steps a)-d)) and subjecting the titanium dioxide scaffold to at least one of the vacuum infiltration steps e)-f) or the double-coating of steps i)-iii). This document is consequently also directed to a recoated or double-coated titanium dioxide scaffold obtainable by or obtained by the method of providing a titanium dioxide scaffold (such as by performing steps a)-d)) and subjecting said titanium dioxide scaffold to at least one of the vacuum infiltration steps e)-g) or the double-coating steps i)-iii).

As mentioned above, the titanium dioxide scaffold is typically provided by performing steps a)-d). In these steps, a first slurry comprising titanium dioxide is applied to a combustible porous structure and allowed to solidify thereon before performing a first sintering at about 400-550° C. for at least 30 min and a second sintering at a temperature of at least 1200° C., such as 1200-1600° C., for at least 10 h to produce a single-coated titanium dioxide scaffold (sintered titanium dioxide scaffold). Steps a)-d) may be performed as disclosed in WO 08/078164. Steps a) and b) may be also be repeated 1-5 times, such as 1, 2, 3, 4 or 5 times before step c) is performed. Repetition of steps a) and b) will reduce the pore diameter of the resulting scaffold.

The combustible porous structure may e.g. be a sponge structure, such as a synthetic sponge. The material the combustible porous structure is made of is preferably an organic material in order to facilitate the removal of the combustible porous structure from the scaffold by combustion. The combustible porous structure may therefore be an organic sponge structure, such as an organic porous polymer sponge, e.g. a polyethylene, silicone, celluloses or polyvinylchloride sponge. One example of a combustible porous structure is a 45 or 60 ppi Bulbren polyurethane foam (Bulbren S, Eurofoam GmbH, Wiesbaden, Germany). The combustible porous structure may be washed with water before providing the first slurry comprising titanium dioxide (herein also denoted first titanium dioxide slurry or first slurry) thereto in order to remove residuals and/or contaminations. The first slurry may be provided to the combustible porous structure by immersing the combustible porous structure in the first slurry. After the immersion, excess slurry may be removed by squeezing and/or centrifuging the combustible porous structure immersed in the first slurry. The first slurry is then allowed to solidify on the porous polymer structure, e.g. by drying the combustible porous structure immersed in the first slurry for at least 5 hours, such as for about 5-24 hours, such as about 10-24 or 15-24 hours, e.g. about 5 hours, 10 hours, 15 hours, 16 hours, 20 hours or 24 hours.

The size and shape of the recoated titanium oxide scaffold may be adjusted by adjusting the size and shape of the combustible porous structure used. Thereby it is possible to produce a scaffold that is tailor-made for a specific intended implantation site of a specific subject. Further, it is possible to use techniques, such as CAD (computer assisted design)

camera techniques, to tailor-make recoated titanium oxide scaffolds for specific applications, such as implants specifically made to fit a certain defect. CAD could be performed both on the combustible porous structure and/or on the titanium dioxide scaffold (before or after the recoating procedure) in order to provide a scaffold with the desired shape. The CAD of a titanium dioxide scaffold which has been subjected to at least one sintering would provide higher accuracy than by performing the CAD on the combustible porous structure. The CAD could e.g. be performed with Nd:YAG laser (J Pascual-Cosp et al.) or by milling.

After solidification of the first slurry on the combustible porous structure, the combustible porous structure is removed from the thereon solidified slurry to obtain a titanium dioxide scaffold structure. This step may be performed as disclosed in WO 08/078164.

The combustible porous structure may be a porous polymer structure and thus removed from the solidified first slurry by heating. Thereby step c) in the above method may e.g. be performed by burning off the combustible porous structure from the solidified first slurry in a slow sintering step. The temperature and time necessary to perform this process will, as the skilled person readily understands, depend on the material that the combustible porous structure is made of. Importantly, the temperature and time should be selected to allow for more or less complete removal of the combustible porous structure. The skilled person will know how to select the necessary time and temperature for a specific combustible porous structure and scaffold to achieve this. The temperature is slowly raised to the desired temperature, such as at 0.2-0.8° C./min, e.g. 0.4-0.6° C./min or about 0.5° C./min. Typically, a temperature of about 400-550° C., such as about 440-510° C., 490-510° C. or 440-460° C., e.g. about 400° C., 450° C., 500° C. or 550° C., is used. This temperature is held for at least 30 min, such as about 30-90 min or 45-75 min, e.g. about 45 min, 60 min, 75 min or 90 min. A titanium dioxide scaffold structure is thereby obtained.

This titanium dioxide scaffold structure is then subjected to a second sintering (step d)) by raising the temperature after the desired holding time in the first sintering step. In this step, the titanium dioxide scaffold structure is subjected to a fast sintering at a higher temperature. This is typically performed at a temperature of at least 1200° C. or at least 1300° C., such as about 1200-1800° C. or 1700-1800° C., e.g. about 1750° C. Typically, the temperature in this second sintering step is raised more rapidly than in the first sintering step, such as at ca 2-5° C./min, e.g. about 3° C./min. The desired temperature is then held for at least 2 hours, such as about 2-45 hours, 5-40 hours, 10-40 hours, 20-40 hours or 10-30 hours. The single-coated titanium oxide scaffold obtained is then allowed to cool to room temperature. This cooling may e.g. be performed at rate of about 2-8° C./min, such as about 2-5° C./min, e.g. about 5° C./min.

After providing a titanium dioxide scaffold such as by performing steps a)-d), the titanium dioxide scaffold may either directly be subjected to the vacuum infiltration of steps e)-g) or double-coated by performing method steps i)-iii).

Steps e)-g) are performed by applying a second slurry comprising titanium dioxide (also denoted second titanium dioxide slurry or second slurry) to the single-coated titanium dioxide scaffold obtained by steps a)-d) or otherwise provided. The second titanium dioxide slurry is then forced into the scaffold by use of vacuum, dried so that the second slurry solidifies and subjected to a third sintering step. The second slurry may be applied to the titanium dioxide scaffold by immersion into the second slurry. The scaffold to which the second slurry has been applied is then subjected to vacuum to force the slurry further into the scaffold structure. This may be performed by placing the scaffold in a vacuum tight glass container and applying a vacuum of at least 0.1 mbar, e.g. about 0.1-0.5 mbar, such as about 0.1-0.3 mbar, e.g. 0.1 mbar, 0.2 mbar, 0.3 mbar, 0.4 mbar or 0.5 mbar for at least about 1 min, such as about 1-10 min, 1-7 min, 3-6 min, 4-6 min or 5 min. Any excess second slurry may then be removed e.g. by careful centrifugation for a few minutes (such as about 0.5-5 min, 1-5 or 1-3 min) at a speed such as about 500-1500 rpm (based on a rotor size suitable for a Biofuge 22R, Heraeus Sepatec centrifuge). Centrifugation after immersion may improve the final result as this results in a more uniform covering of the struts without blocking the pore windows. The second slurry is then allowed to solidify on the scaffold for at least 5 hours, such as for about 5-24 hours, such as about 10-24 or 15-24 hours, e.g. about 5 hours, 10 hours, 15 hours, 16 hours, 20 hours or 24 hours. The scaffold is then subjected to a third sintering at a temperature of at least 1100° C., such as about 1100-1800° C., 1200-1600° C., 1400-1600° C., e.g. at 1400° C., 1500° C. or 1600° C. The time for the third sintering is typically about at least 2 hours, such as about 2-15 hours, 2-10 hours, 2-8 hours, 3-5 hours or about 3 hours or 4 hours. The temperature is raised at ca 2-5° C./min, e.g. about 3° C./min, while the cooling rate for cooling down to room temperature is about 2-8° C./min, such as about 2-5° C./min, e.g. about 5° C./min.

As mentioned above, double coating steps i)-iii) may be performed before steps e)-g) or thereafter. For double coating, a third slurry comprising titanium dioxide (also denoted a third titanium dioxide slurry or third slurry) is applied to the scaffold e.g. by immersion into the third slurry. Any excess third slurry may then be removed e.g. by careful centrifugation for a few minutes (such as about 0.5-5 min, 1-5 or 1-3 min) at a speed such as about 500-1500 rpm (based on a rotor size suitable for a Biofuge 22R, Heraeus Sepatec centrifuge). Centrifugation after immersion may improve the final result as this results in a more uniform covering of the struts without blocking pore windows. The third slurry is then allowed to solidify on the scaffold for at least 5 hours, such as for about 5-24 hours, such as about 10-24 or 15-24 hours, e.g. about 5 hours, 10 hours, 15 hours, 16 hours, 20 hours or 24 hours. The scaffold is then subjected to a further sintering at a temperature of at least 1100° C., such as about 1100-1800° C., 1200-1600° C., 1400-1600° C., e.g. at 1400° C., 1500° C. or 1600° C. The time for this further sintering is typically at least 2 hours or at least 10 hours, such as 2-50 hours, 5-40 hours, 10-50 hours, 10-30 hours, 20-50 hours, or 20-40 hours, e.g. 10 hours, 20 hours, 25 hours, 30 hours, 35 hours, 40 hours, or 45 hours. The temperature is raised at ca 2-5° C./min, e.g. 3° C./min, while the cooling rate for cooling down to room temperature is about 2-8° C./min, such as about 2-5° C./min, e.g. about 5° C./min.

The titanium oxide powder used for preparing the first, second and third titanium dioxide slurries may be in the amorphous, anatase, brookit or rutile crystal phase. The titanium dioxide powder may be precleaned with NaOH (e.g. 1 M NaOH) to remove contaminations, such as contaminations of secondary and tertiary phosphates. Alternatively, if titanium dioxide powder free of contaminations of secondary and/or tertiary phosphates is desirable, titanium dioxide powder free of such contaminations is commercially available (e.g. the titanium oxide from Sachtleben). It may be advantageous to use a titanium dioxide powder having at the most 10 ppm of contaminations of secondary and tertiary phosphates. By using titanium dioxide containing less than about 10 ppm of contaminations of secondary and/or tertiary phosphates when preparing the slurry, the titanium dioxide particles are small enough to allow a proper sintering without the addition of organic antiagglomerating compounds and/or surfactants. The titanium dioxide slurries typically have a pH value of about 1.0 to 4.0, preferably about 1.5-2.0, in order to avoid coagulation and to control the viscosity. The pH of the slurry is preferably kept at this pH for the entire duration of dispersion of the titanium dioxide powder in solvent with small additions of HCl (such as 1 M HCl). It is preferable to reduce the size of the titanium dioxide particles as close as possible to the pH value which gives the theoretical isoelectric point of titanium oxide. For $TiO_2$ this pH value is 1.7. The mean particle size of the titanium dioxide particles may be 10 μm or less, such as 1.4 μm or less. The titanium oxide particles may be monodispersed. The titanium dioxide powder is typically dispersed in water (under stirring and the pH readjusted by the addition of an acid, such as HCl) to prepare a titanium dioxide slurry. The stirring may be continued after all titanium dioxide powder is dispersed, such as for about 2-8 hours. The slurry is e.g. dispersed with a rotational dispermat with metal blades, preferably titanium blades. For example the stirring may be performed at a speed of at least 4000 rpm and for at least 4 hours, such as at 5000 rpm for 5 hours or longer. The pH of the slurry is regularly adjusted to the chosen pH value for adequate zeta potential of the suspension.

The titanium dioxide slurries typically have different concentrations of titanium dioxide in order to have different viscosities. The first slurry typically has a concentration of about 2000-5000 mg/ml of titanium dioxide, such as about 2500-4000 mg/ml, 3000-3500 mg/ml or about 3250 mg/ml. The concentration of titanium dioxide in the second slurry is typically about 200-1000 mg/ml, such as about 300-900 mg/ml, 400-800 mg/ml, 500-600 mg/ml, e.g. about 400 mg/ml, 500 mg/ml, 600 mg/ml, 700 mg/ml or 800 mg/mi. The concentration of titanium dioxide in the third slurry is typically about 1200-1800 mg/ml, such as about 1300-1700 mg/ml, 1500-1700 mg/ml, e.g. 1400 mg/ml, 1500 mg/ml, 1600 mg/ml or 1700 mg/ml.

As is demonstrated in Example 1, the sintering time used in step d) has a large impact on the scaffold structure and compressive strength. With increasing sintering times, the hollow appearance of the struts was changed due to partial elimination of the triangular voids with the struts. This elimination of internal strut porosity appeared to occur by inward collapse of one of the three titanium dioxide strut walls. This collapse led to the formation of cracks and voids at the points where three or more struts join together. Further increasing the sintering time resulted in a reduction of flaw size and number, the struts thereby taking a solid triangular structure with rounded corners. No statistical difference in the pore architectural parameter of the scaffolds occurred during increasing sintering times. However, the compressive strength was markedly increased by the use of longer sintering times. Therefore, by increasing the sintering time of the first sintering (step d)), the strength of the scaffolds can be increased.

Also as demonstrated in Example 1, double coating and vacuum infiltration further increased the compressive strength of the scaffolds. Vacuum infiltration was for example demonstrated to almost double the compressive strength of a double-coated scaffold.

Although not wishing to be bound by theory, this increase in compressive strength appear to be the result of the double coating and/or vacuum infiltration procedures improving the strut uniformity by the second and third slurries depositing in the voids and folds of the struts.

Curiously, reversing the order of the double coating and vacuum infiltration processes caused no significant alterations in the pore architectural characteristics of the recoated titanium dioxide scaffolds or their compressive strength. It appears that the low viscosity second titanium dioxide slurry, used in the vacuum infiltration process, is deposited mainly in the micropores and small voids of the struts, while the optional centrifugation process effectively removes the excess slurry from the scaffold, leaving only a very thin coating on the strut surface. Due to the low viscosity of the second slurry it can be forced into the remaining small flaws in the strut structure with the aid of vacuum, while the thicker third slurry, used for double coating, is deposited in the larger folds of the struts. A negligible increase in strut size due to the vacuum infiltrated coating is likely to arise from blockage of some of the smallest pore windows and accumulation of the second slurry at the strut junctures, which also caused the slight drop in the interconnectivity of the foam structure (see FIG. 5b). This reduction in the interconnectivity of the pore network was more pronounced when the vacuum infiltrated scaffolds were double-coated with the thicker third slurry, indicating that a DC+VI process results in less blocked pore openings than applying the same procedures in reversed order (VI+DC). Nonetheless, the additional vacuum infiltrated low viscosity coating (the second slurry) appears to be an effective method for improving the structural uniformity of a titanium dioxide scaffold, and thus significantly enhancing the mechanical strength of the scaffolds while still maintaining appropriate pore architectural features.

Figure 4:
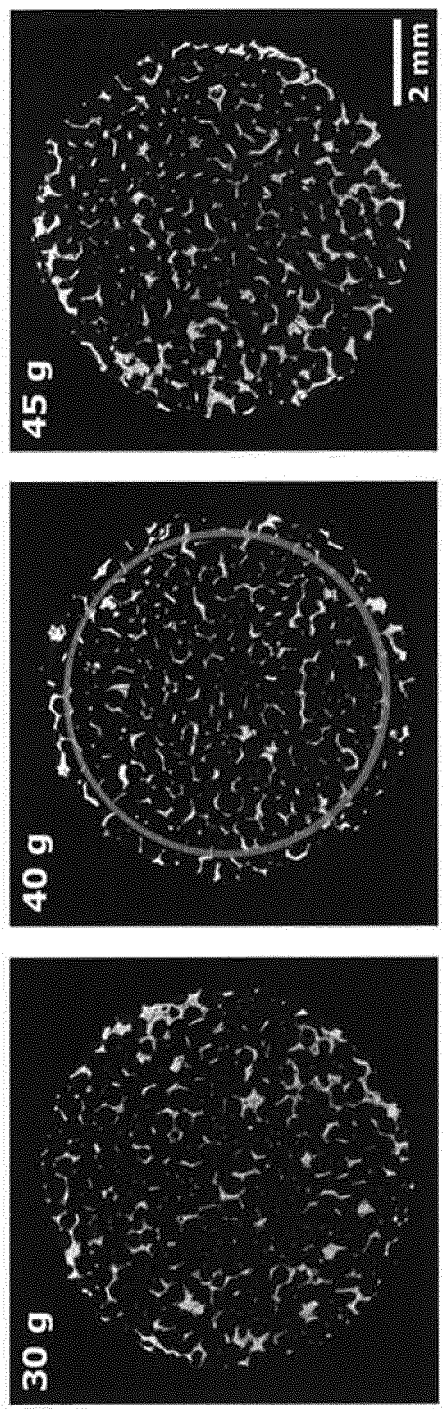
FIG. 4 shows how the solid content of the third slurry used for double coating influenced the uniformity of the $TiO_2$ foam structure: low solid content slurry had low viscosity which resulted in less reproducibility in comparison to slurries with 35-40 g $TiO_2$ powder, whereas higher solid contents (45 g $TiO_2$ powder) resulted into too viscous slurry that did not infiltrate uniformly throughout the scaffold interior. Circle in 40 g $TiO_2$ powder image depicts the VOI selection for 3D analysis.

Since the low viscosity second slurry used for the vacuum infiltration in steps e)-g) appears to only have a negligible effect on the scaffold structure, the pore architectural characteristics are mainly dependent on the higher viscosity third slurry used in steps i)-iii). As the interconnectivity of the pore volume has been identified as one of the most important characteristics for a bone scaffold, the number of blocked pore windows is preferably minimized in the scaffold by optimization of the procedure. Viscosity of the third slurry used for double-coating the scaffolds (DC) had a notable influence on the uniformity of the $TiO_2$ foam structure with both low (30 g) and high (45 g) solid contents causing blockage of the pore windows (FIG. 4), and thereby influencing the interconnectivity of the pore network (FIG. 5b). Since the poor infiltration of the more viscous third slurry resulted in blocked pore openings mainly at the outer edges of the $TiO_2$ foam, the effect of this blockage was not manifested in the 3D interconnectivity analysis as the selected VOI excluded the outermost region of the scaffold cylinder. However, the blockage of the outer pore windows is likely to significantly hinder the cell and tissue penetration towards the scaffold interior and is therefore particularly undesirable. Controlling the viscosity of the third slurry was therefore identified as one of the most important processing parameters governing the uniformity and interconnectivity of the pore network when the mechanical integrity of titanium dioxide scaffolds is improved by a recoating procedure.

The mechanical strength (compression strength) of the recoated titanium dioxide scaffolds produced in accordance with the present document is typically about 1-5 MPa, such as 3-5 MPa. However, as is clear to a person skilled in the art, the compression strength of a recoated titanium dioxide scaffold depends on its porosity. The above mentioned compression strength values are given for a recoated titanium dioxide scaffold having about 90% porosity. Independently on the porosity of a titanium dioxide scaffold, by subjecting the scaffold to the recoating procedure disclosed herein, the compression strength is markedly increased. The compression strength of a scaffold may be determined by performing compression tests in accordance with DIN EN ISO 3386 (e.g. as disclosed in Example 1).

The recoated titanium dioxide scaffold may be used for implantation into a subject, i.e. used as a medical implant. The recoated titanium dioxide scaffold comprises a porous structure with improved surface properties which enhances its biocompatibility and stimulates the growth of cells and attachment of the implant. The porous structure allows ingrowth of cells into the scaffold, which thereby allows for the regeneration of tissue. The large surface area of the recoated titanium dioxide scaffold also facilitates the growth of cells into the structure and thereby the attachment of the scaffold and regeneration of tissue. As the recoated titanium dioxide scaffold is made of a material which in itself has a good biocompatibility, adverse reactions to the scaffold when implanted into a subject are reduced.

The recoated titanium dioxide scaffold is macroporous and comprises macropores and interconnections. The macropores have a pore diameter in the range of between approximately 10-3000 µm, such as about 20-2000 µm, 30-1500 µm or 30-700 µm. The macropore diameter may be above about 100 µm or about 30-700 µm. For bone, the pore diameter is optimally about 30-100 µm. However, it is important that the scaffold also allows for the ingrowth of larger structures such as blood vessels and trabecular bone, i.e. also has pores of about 100 µm or more. It is important that at least some of the pores of the scaffolds are interconnected.

The pore diameter (pore size) may be adjusted by the choice of structure used for producing the scaffold, e.g. the choice of sponge and the number of times this structure is dipped into the first slurry comprising titanium dioxide. By altering the pore diameter one may affect the rate and extent of growth of cells into the recoated titanium dioxide scaffold and therefore the constitution of the resulting tissue.

It may be preferable that the pores are interconnective or partially interconnective. This means that the pores are not pores with a "dead end" or closed pores, but that they have at least two open ends allowing for the passage of nutrients and waste products in more than one direction. Thereby, the risk that necrotic tissue forms is reduced. The macroporous system preferably occupies at least 50% volume of the scaffold. The volume of the macro- and micropores in the recoated titanium dioxide scaffolds may vary depending on the function of the scaffold. If the aim with a treatment is to replace much bone structure and the recoated titanium dioxide scaffold can be kept unloaded during the healing time, the recoated titanium dioxide scaffold may be made with a macroporous system occupying up to 90% of the total scaffold volume, It may be preferred that a recoated titanium dioxide scaffold has a total porosity of about 40-99%, preferably 70-90% or 80-90%.

The fractal dimension strut of the recoated titanium dioxide scaffold is typically about 2.0-3.0, such as about 2.2-2.3. The strut thickness affects the strength of the scaffolds, the thicker the struts in the scaffold are, the stronger is the scaffold.

The recoated titanium dioxide scaffolds essentially lack an inner strut volume, which can be observed by the filled up cross section in SEM.

It will be understood by those of skill in the art that the surface of the recoated titanium dioxide scaffold also has a structure on the microlevel and the nanolevel. This micro and nano structure may be modified due to the manufacturing conditions. The pores created by the manufacturing process are on the microlevel in the range of about 1-10 µm. The pores on the nanolevel are less than 1 µm in diameter.

A recoated titanium dioxide scaffold typically has a combined micro and macro pore diameter of approximately 10-3000 µm, such as 20-2000 µm, 30-1500 µm or 30-700 µm. The pore diameter may be above 40 µm, with interconnective pores of at least 20 µm.

The recoated titanium dioxide scaffolds have a structure of hollow tubules in which the bone will grow and create the interconnecting bone trabeculae. Cells will grow both on the inside and the outside of these tubules.

Also, biomolecules may be provided to the surface of the recoated titanium dioxide scaffolds. If biomolecules are to be provided to the recoated titanium dioxide scaffold, these may be provided after all recoating steps are finalized. The presence of biomolecules may further increase the biocompatibility of the recoated titanium dioxide scaffolds and rate of cell growth and attachment. Biomolecules comprise in the present context a wide variety of biologically active molecules including natural biomolecules (i.e. naturally occurring molecules derived from natural sources), synthetic biomolecules (i.e. naturally occurring biomolecules that are synthetically prepared and non-naturally occurring molecules or forms of molecules prepared synthetically) or recombinant biomolecules (prepared through the use of recombinant techniques). Examples of biomolecules of interest include, but are not limited to biomolecules disclosed in US 2006/0155384, such as bioadhesives, cell attachment factors, biopolymers, blood proteins, enzymes, extracellular matrix proteins and biomolecules, growth factors and hormones, nucleic acids (DNA and RNA), receptors, synthetic biomolecules, vitamins, drugs, biologically active ions, marker biomolecules, etc., including proteins and peptides such as statins and proteins or peptides that stimulate biomineralization and bone formation. Other examples of biomolecules include inorganic, biologically active ions, such as calcium, chromium, fluoride, gold, iodine, iron, potassium, magnesium, manganese, selenium, sulphur, stannum, silver, sodium, zinc, strontium, nitrate, nitrite, phosphate, chloride, sulphate, carbonate, carboxyl or oxide. The biomolecules may e.g. be attached to the surface of the titanium dioxide scaffold via dipping into a solution comprising the biomolecule or via an electrochemical process, such processes being known by the skilled person and e.g. disclosed in WO02/45764 or WO03/086495.

The present document is also directed to a medical prosthetic device comprising a recoated titanium dioxide scaffold as defined herein. A medical prosthetic device may be a recoated titanium dioxide scaffold in itself. Alternatively, the medical prosthetic device may comprise a recoated titanium dioxide scaffold in combination with another structure, such as orthopaedic, dental or any other fixating devices or implants. This document is therefore also directed to a recoated titanium dioxide scaffold or a medical prosthetic device comprising a recoated titanium dioxide scaffold for the regeneration, repair, substitution and/or restoration of tissue, in particular bone tissue.

The recoated titanium dioxide scaffold may be implanted into a subject wherein cells will grow into the scaffold structure. It is also possible to seed and grow cells on the scaffold prior to implantation. The interconnected macroporous structure of the recoated titanium dioxide scaffold is especially suitable for tissue engineering, and notably bone tissue engineering, an intriguing alternative to currently available bone repair therapies. In this regard, bone marrow-derived cell seeding of the recoated titanium dioxide scaffold is performed using conventional methods, which are well known to those of skill in the art (see e.g. Maniatopoulos et al. 1988). Cells are seeded onto the recoated titanium dioxide scaffold and cultured under suitable growth conditions. The cultures are fed with media appropriate to establish the growth thereof.

As set out above, cells of various types can be grown throughout the present recoated titanium dioxide scaffold. More precisely, cell types include hematopoietic or mesenchymal stem cells, and also include cells yielding cardiovascular, muscular, or any connective tissue. Cells may be of human or other animal origin. However, the recoated titanium dioxide scaffold is particularly suited for the growth of osteogenic cells, especially cells that elaborate bone matrix. For tissue engineering, the cells may be of any origin. The cells are advantageously of human origin. A method of growing cells in a three dimensional recoated titanium dioxide scaffold allows seeded osteogenic cells, for example, to penetrate the metal oxide scaffold to elaborate bone matrix, during the in vitro stage, with pervasive distribution in the structure of the recoated titanium dioxide scaffold. Osteogenic cell penetration and, as a result, bone matrix elaboration can be enhanced by mechanical, ultrasonic, electric field or electronic means The recoated titanium dioxide scaffold is useful whenever one is in need of a structure to act as a framework for growth of cells, such as for regeneration, repair, substitution and/or restoration of a tissue. The recoated titanium dioxide scaffold is particularly useful for the regeneration, repair, substitution and/or restoration of bone and/or cartilage structures. Examples of situations where the regeneration of such structures may be necessary include trauma, surgical removal of bone or teeth or in connection to cancer therapy.

Examples of structures in a subject which wholly or partially may be replaced include, but are not limited to, cranio-facial bones, including arcus zygomaticus, bones of the inner ear (in particular the malleus, stapes and incus, maxillar and mandibular dentoalveolar ridge, walls and floor of eye sockets, walls and floor of sinuses, skull bones and defects in skull bones, socket of hip joint (Fossa acetabuli), e.g. in the case of hip joint dysplasias, complicated fractures of long bones including (but not restricted to) humerus, radius, ulna, femur, tibia and fibula, vertebrae, bones of the hands and feet, finger and toe bones, filling of extraction sockets (from tooth extractions), repair of periodontal defects and repair of periimplant defects.

In addition, the recoated titanium dioxide scaffold is useful for the filling of all types of bone defects resulting from (the removal of) tumors, cancer, infections, trauma, surgery, congenital malformations, hereditary conditions, metabolic diseases (e.g. osteoporosis and diabetes).

This document is therefore also directed to a recoated titanium dioxide scaffold as defined herein for use as a medical prosthetic device.

The present document is further directed to a method for the regeneration, repair, substitution and/or restoration of tissue, such as bone, comprising the implantation into a subject in need thereof of a recoated titanium dioxide scaffold or a medical prosthetic device comprising a recoated titanium dioxide scaffold.

The recoated titanium dioxide scaffold may also be used for the regeneration, repair, substitution and/or restoration of tissue. This document is therefore also directed to the use of a recoated titanium dioxide scaffold or a medical prosthetic device comprising a recoated titanium dioxide scaffold for the regeneration, repair, substitution and/or restoration of tissue. Further disclosed is a recoated titanium dioxide or a medical prosthetic device comprising a recoated titanium dioxide scaffold for use for the regeneration, repair, substitution and/or restoration of tissue. Also, this document is directed to the use of a recoated titanium dioxide scaffold for the preparation of a medical prosthetic device for the regeneration, repair, substitution and/or restoration of tissue.

The high compression strength of the recoated titanium dioxide scaffold also enables new uses of the scaffold in load bearing bone structures. Previously available scaffolds generally are too weak to be used in such applications. However, due to the higher compression strength of the recoated titanium dioxide scaffold disclosed herein, it is now possible to implant the scaffold into bone structures, such as spine, femur, tibia, with high load bearing. It also allows for placement in larger defects than today's bone graft substitutes. Also, the number of surgical operations may be reduced and bone healing increased.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

The invention will be further described in the following examples, which do not limit the scope of the invention described in the claims.

EXPERIMENTAL SECTION

Example 1

Materials and Methods
Sample Preparation

Polymer sponge replication method was used to produce the reticulated ceramic foam scaffolds. Ceramic slurry was prepared by gradual addition of 65 g of the ceramic $TiO_2$ powder (Kronos 1171, Kronos Titan GmbH, Leverkusen, Germany; precleaned with 1 M NaOH) in total to 25 ml of sterilized water. In order to avoid coagulation and to control the viscosity, the pH of the slurry was kept at 1.5 for the entire duration of stirring with small additions of 1 M HCl. After dispersing the $TiO_2$ powder in water, stirring was continued for 2.5 h at 5000 rpm (Dispermat Ca-40, VMA-Getzmann GmbH, Reichshof, Germany). For more details of the polymer sponge replication method, see Tiainen H et al. 2010.

Cylindrical polyurethane foam templates (60 ppi, Bulbren S, Eurofoam GmbH, Wiesbaden, Germany), 10 mm in both diameter and height, were coated with the prepared slurry. Excess slurry was squeezed out of the foam templates between two polymer foam sheets. The samples were then placed on a porous ceramic plate and allowed to dry at room temperature for at least 16 h before sintering. For the burnout of the polymer, the scaffolds were slowly heated to 450° C. at a heating rate of 0.5° C./min. After 1 h holding time at 450° C., the temperature was raised to 1500° C. at a rate of 3° C./min and the sintering time at this temperature was set to 2-40 h (HTC-08/16, Nabertherm GmbH, Lilienthal, Germany). The sintered scaffolds were then cooled back to room temperature at the cooling rate of 5° C./min providing a single-coated titanium dioxide scaffold (SC scaffold).

Some of the single-coated titanium dioxide scaffolds produced by the above replication method (sintered for 40 h) were double-coated (DC) with TiO$_2$ slurry containing 40 g of powder dispersed in 25 ml of sterilized water and prepared as described above. The pH was adjusted to 1.5 for the entire duration of stirring. The SC scaffolds were immersed in the prepared slurry and excess slurry was removed from the foam structure by centrifugation (1 min @ 1000 rpm; Biofuge 22R Heraeus Sepatech, Osterode, Germany) to ensure that the TiO$_2$ slurry covered the surface of the foam struts uniformly without blocking the pore windows. After 16 h of drying, sintering of the foams was performed by raising the temperature to 1500° C. at a rate of 3° C./min and the setting the sintering time at this temperature to 40 h. The sintered scaffolds were then cooled back to room temperature at the cooling rate of 5° C./min.

Some of the double-coated scaffold samples were then further coated with a low viscosity slurry containing 10-20 g of the cleaned TiO$_2$ powder dispersed in 25 ml of sterilized water and prepared as described above. The scaffold samples were immersed in the slurry and subjected to a vacuum infiltration (VI) process. The slurry infiltrated scaffolds were placed in a vacuum tight glass container and vacuum of 0.2 mbar was applied for 5 minutes. Following the vacuum infiltration, the removal of the excess slurry was performed with centrifugation as described above. After 16 h drying period in room temperature, the coated scaffolds were sintered at 1500° C. for 4 h before being cooled back to room temperature at 5° C./min cooling rate, while the heating rate was set to 3° C./min. The order of the two procedures (DC and VI) was reversed for some of the scaffold samples.

Slurry Rheology

The rheological properties of the prepared TiO$_2$ slurries were evaluated using a Bohlin Visco 88 viscometer (Malvern Instruments Ltd, Malvern, UK) using cup and bob geometry (C 25) at 20° C. Viscosity of the TiO$_2$ slurry was measured at shear rate interval 2.5-100 s-1 with both increasing and decreasing shear rates.

Pore Architectural Characterization

The initial visualization and optical observation of the microstructure of the prepared scaffolds was performed using a scanning electron microscope (TM-1000, Hitachi High-Technologies, Japan). The samples were mounted on aluminum stubs with conductive carbon tape and viewed with backscattered electrons at 15 kV accelerating voltage.

Micro-computed tomography was used to determine the three-dimensional microstructure of the scaffolds. The samples were mounted on a plastic sample holder and scanned with desktop 1172 micro-CT imaging system (Sky-Scan, Aartselaar, Belgium) at 6 µm voxel resolution using source voltage of 100 kV and current of 100 µA with 0.5 mm aluminum filter. The samples were rotated 180° around their vertical axis and three absorption images were recorded every 0.4° of rotation. These raw images of the samples were reconstructed with the standard SkyScan reconstruction software (NRecon) to serial coronal-oriented tomograms using 3D cone beam reconstruction algorithm. For the reconstruction, beam hardening was set to 20% and ring artifact reduction to 12. The image analysis of the reconstructed axial bitmap images was performed using the standard SkyScan software (CTan and CTvol) and included thresholding and despeckling (removing objects smaller than 500 voxels and not connected to the 3D body). In order to eliminate potential edge effects, a cylindrical volume of interest (VOI) with a diameter of 8 mm and a height of 3 mm was selected in the center of the scaffold. The porosity was then calculated as 100%-vol. % of binarised object in the VOI.

All images underwent 3D analysis, followed by the quantification of interconnectivity using the 'shrink-wrap' function, which allows measuring the fraction of pore volume in a scaffold that is accessible from the outside through openings of a certain minimum size (Moore et al. 2004). A shrink-wrap process was performed between two 3D measurements to shrink the outside boundary of the VOI in a scaffold through any openings the size of which is equal to or larger than a threshold value (0-160 µm were used in this study). Interconnectivity was calculated as follows:

$$\text{Interconnectivity} = \frac{V - V_{shrink-wrap}}{V - V_m} \times 100\%,$$

where V is the total volume of VOI, $V_{shrink-wrap}$ is the VOI volume after shrink-wrap processing, and $V_m$ is the volume of scaffold material.

The mean strut and pore diameter distributions for each scaffold sample were found by measuring the material thickness and material separation on reconstructed binarised dataset, respectively, Additional noise was again removed using the 'despeckling' function, which removed all objects smaller than 500 voxels and not connected to the 3D body.

Compressive Strength

The mechanical strength was investigated in a compressive test (Zwicki, ZwickRoell, Ulm, Germany). The compression tests were performed in accordance with DIN EN ISO 3386 at room temperature using a load cell of 1 kN with preloading force set to be 0.5 N. The scaffolds were compressed along their long axes at a compression speed of 100 mm/min until failure. The force and displacement were recorded throughout the compression and converted to stress and strain based on the initial scaffold dimensions.

Statistical Analysis

Normality and equal variance tests were performed prior to further statistical testing. Statistical comparison of different data groups was performed using Student's t-test or one-way analysis of variance (ANOVA) test followed by post hoc tests for pairwise comparisons performed using Hoim-Sidak method. Statistical significance was considered at a probability $p<0.05$ and n=10 unless otherwise specified. A correlation study was performed with a bivariate regression analysis, Spearman Rank Order correlation. The results were interpreted as follows: small correlation if $0.1<|\rho|<0.3$; medium correlation if $0.3<|\rho|<0.5$; strong correlation if $0.5<|\rho|<1$ and $p<0.05$ [22]. A negative $\rho$ indicated a negative correlation, whereas a positive $\rho$ indicated a positive correlation ($\rho$=Spearman's rank correlation coefficient). All statistical analysis was performed using software SigmaPlot 12 (Systat Software Inc, San Jose, USA).

Results

Effect of Sintering Time on Scaffold Structure and Compressive Strength

Figure 1B:
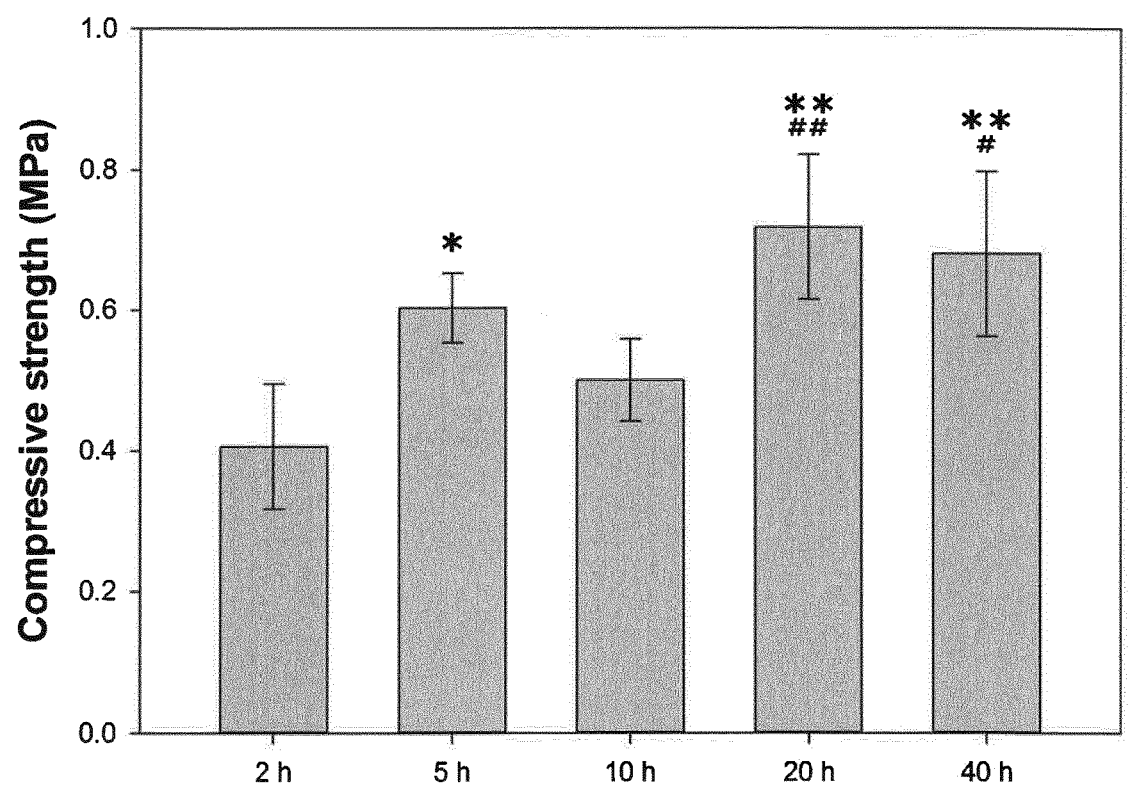

The typical microscopic appearances and compressive strengths of the SC TiO$_2$ scaffolds after various sintering times are presented in FIG. 1. After a sintering time of 2 h at 1500° C., the TiO$_2$ foam struts had the typical hollow appearance of foams prepared using the replication process. Finer-scale microporosity was also apparent as small longitudinal ruptures on some of the strut walls and occasional lateral cracks on the strut edges. As the sintering time was increased to 5 hours, the triangular voids within the ceramic struts were partially eliminated from approximately 50% of the foams struts. This elimination of the internal porosity occurred by inward collapse of one of the three $TiO_2$ strut walls resulting in a folded strut appearance with a V-shaped cross-section of thin $TiO_2$ edges (FIG. 1; 5 h-10 h). The collapse of the hollow strut structure also led to appearance of large cracks and voids at the stems of the foams where three or more struts join together. Such large flaws were also found in the majority of collapsed struts present in the $TiO_2$ foams sintered for 10 h. After 10 h of sintering at 1500° C. almost all of the struts had undergone strut folding, while further increase in sintering time at the same temperature resulted in marked reduction in the flaw size and number. In both 20 h and 40 h groups, majority of the folded struts had developed a solid triangular structure with rounded corners and the earlier rather distinct V-shaped structure of the folded struts disappeared (FIG. 1; 40 h). The large voids at the junctures of $TiO_2$ struts as well as longitudinal cracks along the strut edges were markedly less frequent observation in the $TiO_2$ scaffolds that were continuously sintered for 20 hours in comparison to the scaffolds prepared with shorter sintering times.

As illustrated in FIG. 1, the overall superficial grain size of $TiO_2$ did not alter markedly during the long sintering times, although the amount of the smallest grains appeared to reduce noticeably as the sintering time increased resulting in more uniform grain size. The $TiO_2$ grains were well-integrated via uniform grain boundaries and the overall grain size was relatively large in all samples. Preferential grain growth of few large grains was also evident in all of the sample groups, particularly close to the strut junctures, while the average grain size in the struts themselves remained markedly smaller. The features of the folded $TiO_2$ struts became observably more rounded as the sintering time was prolonged from 5 h to 20 h, and the outer edges of the superficial $TiO_2$ grains became more three-dimensional resulting in an increased height difference at superficial grain boundary regions in comparison to the more planar strut microstructure that underwent shorter sintering procedure in 1500° C. No apparent changes occurred in the scaffold microstructure as the sintering time was further increased to 40 h.

Increasing sintering time had no significant influence on the pore architectural parameters of the SC $TiO_2$ scaffolds, although the porosity appeared somewhat reduced following 40 h sintering while a shift towards larger average strut size values was observed due to longer sintering times at 1500° C. However, no statistically significant difference was observed in the pore architectural parameters of the $TiO_2$ scaffold groups, whereas the compressive strength of the $TiO_2$ scaffolds was found to strongly correlated with increasing sintering time ($\rho=0.592$, $p<0.01$). In addition, the overall dimensions of the $TiO_2$ scaffold cylinders were found to diminish slightly as the sintering time increased.

Figure 2A:
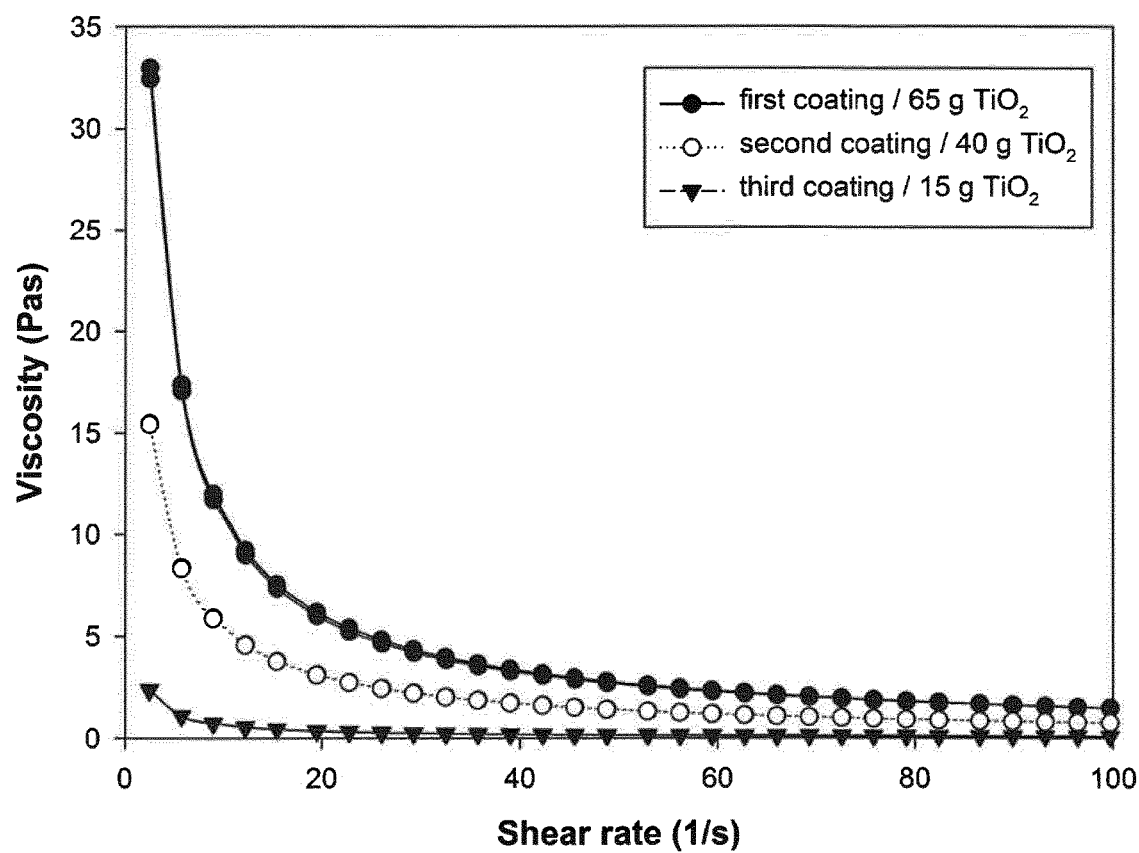
FIG. 2 shows the viscosity as a function of shear rate for the $TiO_2$ slurries used in the scaffold production. (a) The difference in viscosity between the slurries used for difference coating procedures, (b-c) effect of solid content on the rheological properties of the $TiO_2$ slurry.
Figure 2B:
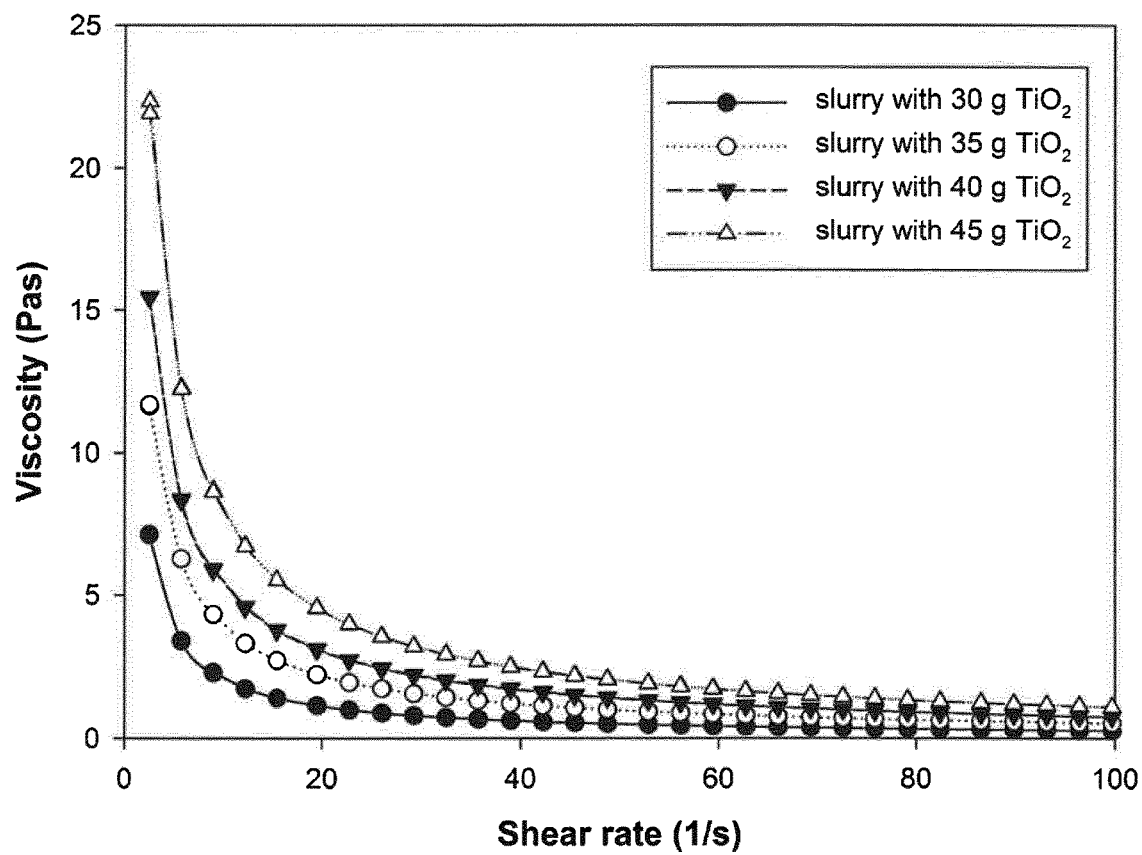
Figure 2C:
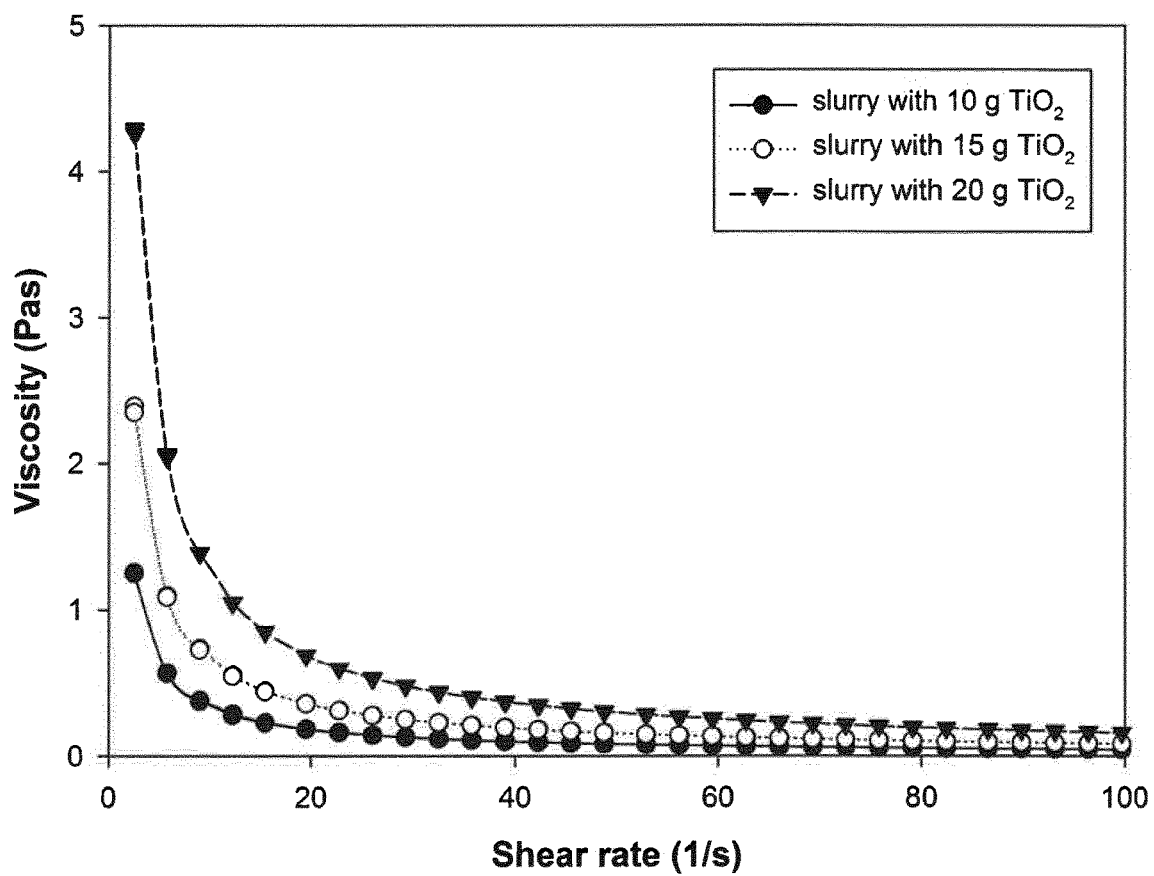

Effect of DC and/or VI Procedures on Scaffold Structure and Compressive Strength Viscosities of the $TiO_2$ slurries used for the coating of the sintered $TiO_2$ foams are plotted as a function of shear rate in FIG. 2. All prepared slurries demonstrated pseudoplastic rheological behaviour. The viscosities of the slurries used in different coating procedures as well as the different slurries prepared for either double-coating (DC) or vacuum-infiltration (VI) with low viscosity slurry showed a marked increase at low shear rates as the solid content increased, while the difference in viscosity became considerably smaller with increasing shear rate.

Figure 3:
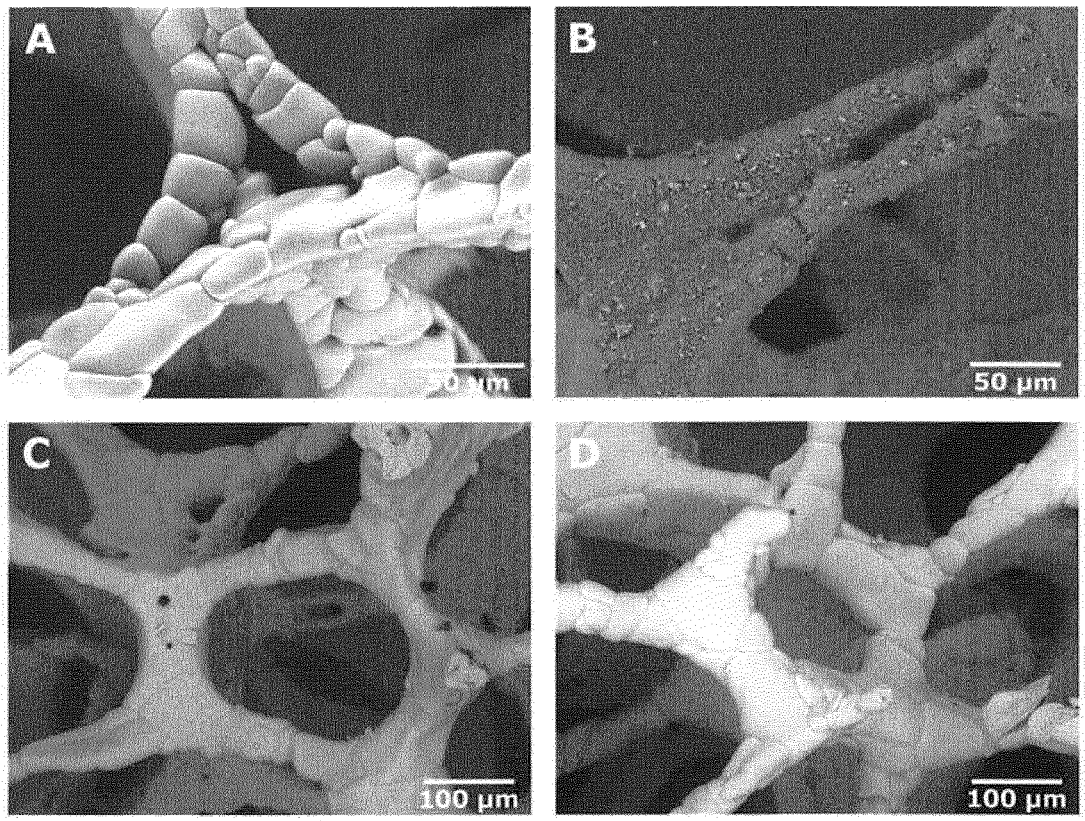
FIG. 3 shows the that the double coating procedure was found to reduce the flaw size and number by filling the micropores and folds remaining in the $TiO_2$ foam struts after the replication process. Vacuum infiltration with low viscosity slurry further improved the uniformity of the strut structure without blocking the macropore windows. (A) Single-coated, (B) double-coated prior to sintering, (C) double-coated after sintering, and (D) double-coated and vacuum infiltrated $TiO_2$ foam after sintering at 1500° C.

Double coating (DC) was found to reduce the flaw size and number in the $TiO_2$ foam struts by partially filling the micropores, voids, and folds remaining in the folded strut structure on the single-coated scaffolds (SC) as illustrated in FIG. 3. DC slurry was deposited to the voids and folds of the struts, while only a thin layer of $TiO_2$ particles covered the rest of the strut surface (FIG. 3b), resulting in only slight increase in the strut thickness and, consequently, somewhat reduced pore size (pore diameter) and overall porosity (Table 1).

TABLE 1

Selected pore architectural parameters of the scaffolds prepared using various procedures (mean ± SD). Statistically significant difference was found between all parameters for recoated groups in comparison to single-coated scaffolds, whereas no difference was observed between the different recoated groups. DC = double-coating, VI = vacuum infiltration.

| Procedure | Porosity % | Pore size μm | Strut size μm |
|---|---|---|---|
| DC 30 g | 89.1 ± 1.6 | 429 ± 22 | 62.7 ± 7.4 |
| DC 35 g | 89.8 ± 1.2 | 453 ± 8 | 64.1 ± 3.7 |
| DC 40 g | 89.8 ± 1.7 | 441 ± 14 | 63.9 ± 6.6 |
| DC 45 g | 90.0 ± 1.0 | 443 ± 10 | 64.9 ± 4.7 |
| DC + VI 10 g | 89.1 ± 1.0 | 443 ± 9 | 70.4 ± 5.3 |
| DC + VI 15 g | 89.5 ± 0.9 | 439 ± 12 | 68.0 ± 3.6 |
| DC + VI 20 g | 88.7 ± 1.4 | 430 ± 13 | 69.3 ± 6.7 |

Vacuum infiltrating the DC scaffolds with low viscosity slurry led to further improvement in the strut uniformity without significant changes in the strut thickness as most of the $TiO_2$ slurry was deposited in the remaining micropores of the foam struts. No significant changes were observed in any of the measured pore architectural parameters between the different groups (DC, DC+VI, or VI+DC). However, the viscosity of the double-coating slurry was found to have an effect on the uniformity of the overall foam structure as illustrated in FIG. 4. While the foams coated with slurry containing 35-40 g of $TiO_2$ powder had a uniform structure throughout the scaffold volume with only a limited number of blocked pore windows, both higher (45 g) and lower (30 g) solid content resulted in a reduction in structural uniformity. Slurries with low solid contents, and thereby reduced viscosity, resulted in increased number of blocked pore windows, whereas high viscosity of the slurry containing 45 g of $TiO_2$ led to poor infiltration of the slurry into the interior regions of the scaffold structure, while the many pores at the outer edges of the scaffolds remained blocked following removal of excess slurry by centrifugation.

Figure 5A:
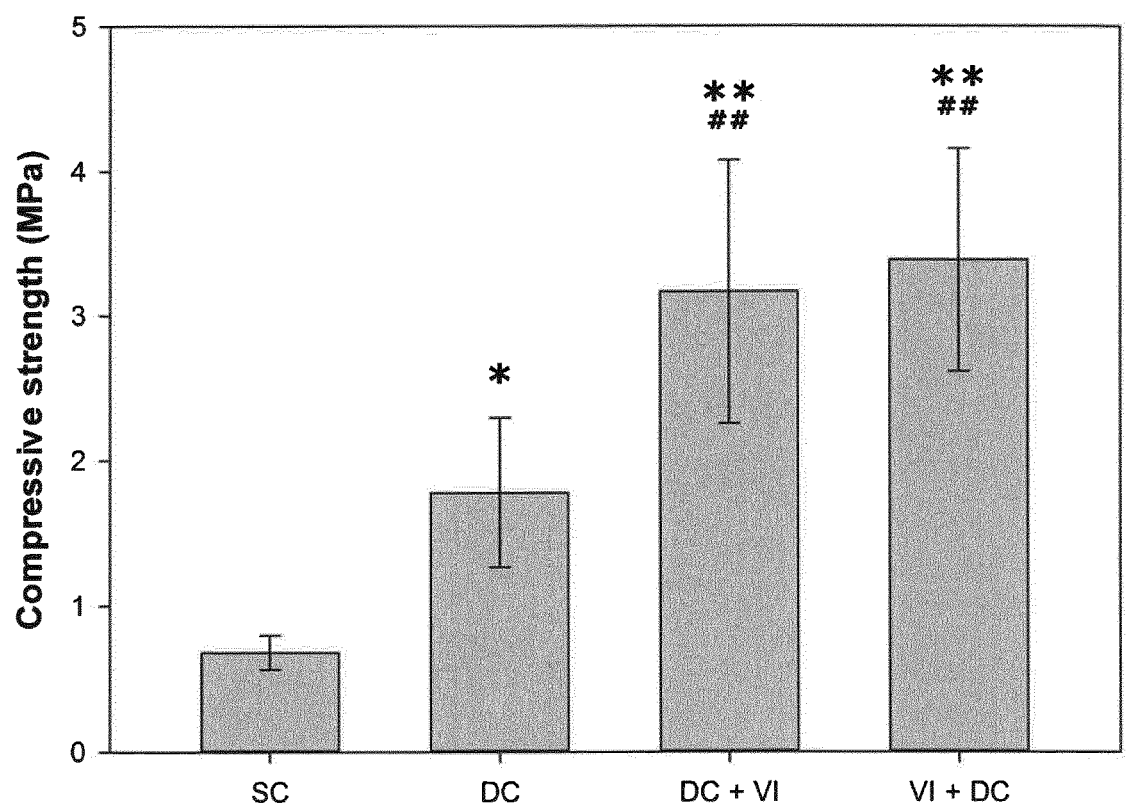
FIG. 5 shows that: (a) The recoating procedure led to significant increase in the compressive strength of the prepared ceramic $TiO_2$ scaffolds. Statistically significant difference in comparison to SC (*,**) and DC (##), *$p<0.05$ and **,##$p<0.01$, n=10. (b) Effect of the DC and VI procedures on the interconnectivity of the pore network. SC=single-coated, DC=double-coated, VI=vacuum infiltration.
Figure 5B:
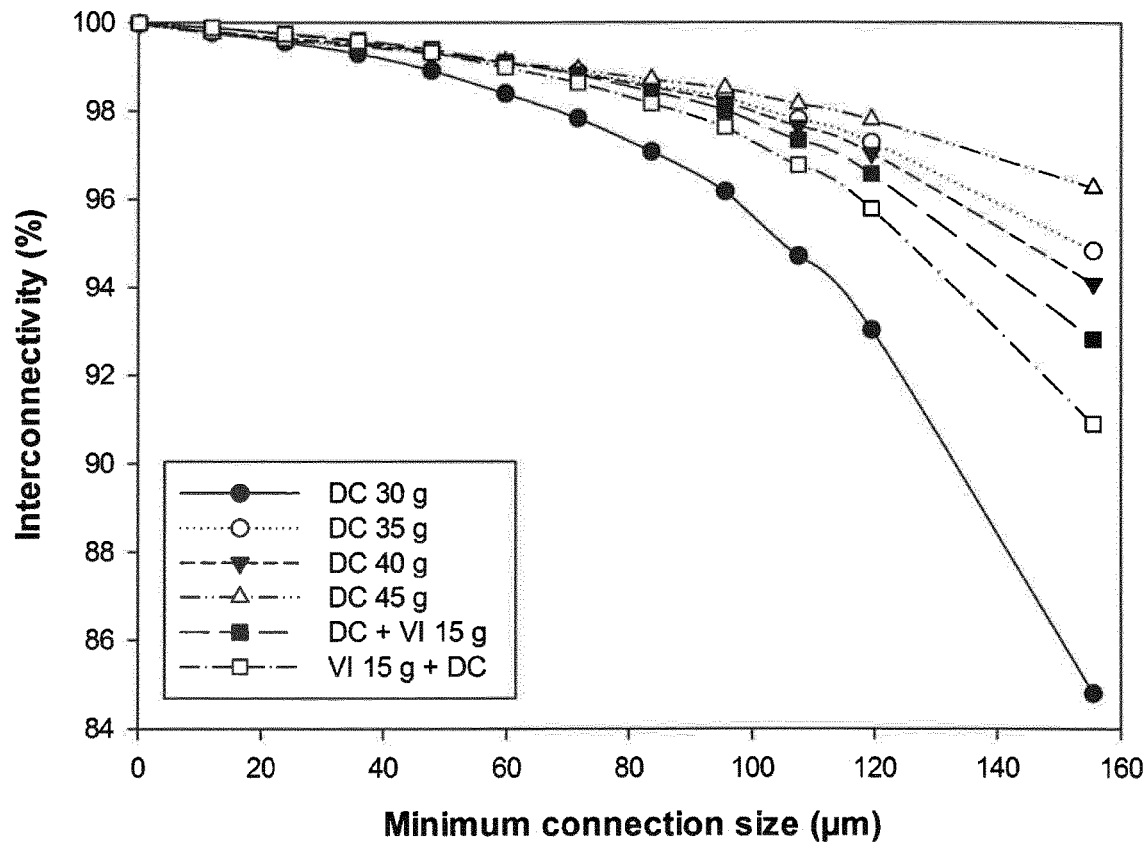

The compressive strength of the porous $TiO_2$ scaffolds was found to increase significantly due to the different procedures (FIG. 5a). The titanium dioxide slurry applied by the vacuum infiltration process was shown to further enhance the compressive strength of the scaffolds as the average strength values increased from 1.78±0.52 MPa for double-coated scaffolds to 3.39±0.77 MPa when the vacuum infiltrated $TiO_2$ coating was applied. However, the interconnectivity of the pore network was slightly reduced due to the low viscosity slurry, although this reduction was only noticeable at interconnections sized above 100 μm (FIG. 5b). Furthermore, also the solid content of the slurry used for double-coating the ceramic foams influenced the interconnectivity of the pore network with lowest solid content resulting in a reduction in interconnectivity while only small differences were observable between the three other DC groups.

DISCUSSION

The presence of pre-existing flaws in the ceramic foam structure may have detrimental effect on the strut strength, and therefore can severely restrict their use in applications where mechanical loading is expected. One crucial factor limiting the compressive strength of reticulated ceramic foams prepared using the polymer sponge replication method is the presence of triangular void within the ceramic foam skeleton. This hollow space within the foam struts is a common feature in foams prepared with this method and corresponds to the space formerly occupied by the sponge template. In addition, the replication process typically results in several lateral cracks alongside the highly curved edges of the foams struts due to the poor slurry coverage at such location and the low resistance of these narrow strut edges to stresses induced by the thermal expansion mismatch of the polymer template and the ceramic coating.

Long sintering times have been previously been shown to result in partial elimination of the triangular pores within the struts of highly porous ceramic $TiO_2$ scaffold structures (Fostad et al. 2009 and Tiainen et al. 2010). Fostad et al. 2009 reported strut folding in $TiO_2$ scaffolds prepared using 45 ppi polymer foam template following 30 h sintering in 1500° C. but they only observed a small correlation between the strength and increasing sintering time. Nevertheless, they recommended exceeding 30 h as such heating schedule led to strut folding in $TiO_2$ foams with pore diameters between 400 µm and 600 µm. However, the mechanism and evolution of the strut folding and subsequent consolidation of the strut structure during the sintering process has not previously been described in detail in the relevant literature.

Typically, the strut walls of replicated ceramic foams appear to be composed of three individual lath-like segments, and often the sintered struts also have longitudinal cracks separating the three strut segments from each other. However, even after 2 h of sintering at 1500° C., the three walls of the struts of prepared $TiO_2$ foams formed a uniform structure and the typical longitudinal cracks at the edges of them were a relatively rare finding. This was due to the high sintering rate of the $TiO_2$ particles, manifested by the large overall grain size of the strut walls observed even after the shorter holding times (2-5 h), at the applied sintering temperature of 1500° C. The densification induced by the high sinterability of $TiO_2$ led to reduction in the initial volume of the hollow strut interior as the corners of the strut walls sintered together, causing one of the three walls to bend inwards.

As the sintering time was increased, the strut folding evolved as an inward collapse of one of the three strut walls, which was typically preceded by a longitudinal rupture of thin concave strut wall (FIG. 1; 2-5 h). By 10 h holding time, virtually all of the foam struts had already underwent full strut folding, thus practically eliminating the hollow space within the strut columns but creating large voids in the junctures where three or more strut columns join together. In combination with the thin V-shaped strut geometry, these large folds and voids at the stem of the struts are likely to have caused the small drop in the strength values of these foams in comparison to those sintered for only 5 hours. Further consolidation of the strut structure during long sintering times (20-40 h) led to solid and round-edged triangular struts as the outer edges of the folded V-shaped struts merged together (FIG. 1), resulting in improved compressive strength due reduced flaw size and enhanced structural uniformity. Interestingly, the strut folding and the subsequent consolidation of the ceramic struts did not result in a reduction in the mean strut thickness as one might have expected. Instead, a slight but not statistically significant increase was observed as the sintering time was increased, whereas the overall porosity appeared to be somewhat reduced (Table 2).

TABLE 2

Selected pore architectural parameters of the scaffolds prepared using various sintering times (mean ± SD). No statistically significant differences were observed between the different scaffold groups. n = 10. Pore size is the pore diameter.

| Sintering | Porosity % | Pore size µm | Strut size µm |
|---|---|---|---|
| 2 h | 94.1 ± 1.3 | 450 ± 9 | 45.8 ± 4.1 |
| 5 h | 93.0 ± 0.8 | 434 ± 5 | 48.1 ± 1.7 |
| 10 h | 93.7 ± 1.5 | 438 ± 11 | 47.3 ± 4.3 |
| 20 h | 93.5 ± 1.3 | 450 ± 6 | 49.6 ± 4.8 |
| 40 h | 92.5 ± 0.4 | 436 ± 16 | 51.1 ± 1.6 |

This apparent increase in the strut diameter may be linked to the consolidation of the overall microstructure with the increasing degree of sintering also resulting in slightly reduced porosity and the overall dimensions of the $TiO_2$ foam cylinders. While the overall size of the superficial grains appeared not to grow markedly during the prolonged sintering, the volume of the $TiO_2$ grains increased drastically as the fraction of smallest grains was consumed by the larger grains, thus facilitating the consolidation of the strut structure. Nonetheless, the further densification in the microstructure that occurred after 20 h of sintering did not appear to have an effect on the mechanical properties of the $TiO_2$ scaffold foams.

Although most of internal void volume was eliminated by the strut folding occurring during prolonged sintering of the $TiO_2$ foams, some inaccessible closed porosity still remains within the strut structure, particularly at the juncture of the foam struts where the volume of the initial hollow void volume had been the largest. However, the increased radius of curvature at the corners of this remaining internal porosity results in lower degree of local stress amplification at the flaw site, which also contributes to the increased compressive strength of the scaffold structure. In addition, the thickness of the ceramic coating is typically larger at the stem of the strut in comparison to the strut columns, and thus the ceramic wall surrounding the blunted edge of the internal void space is more resistant to fracture than the thin walls of the hollow struts in samples sintered for <10 h, which also contributes to the increased strength of the samples sintered from 20-40 h. The use of sintering times of about 20-40 hours may therefore preferably be used in the method for providing a recoated titanium dioxide scaffold of the present document. Furthermore, applying a thicker ceramic coating on the polymer template ought to result in thicker, and thereby stronger, folded struts.

Nevertheless, it was surprisingly found that the major advantage of the inward collapse of the walls of the hollow struts is the fact that the formerly nearly inaccessible pore volume within the ceramic foam skeleton is for most part eliminated or made accessible for recoating procedure. While the strut folding itself led to significant enhancement in the compressive strength of the prepared $TiO_2$ scaffolds, the strength of these single-coated scaffolds remained well lower limit of the strength of healthy trabecular bone (<<2 MPa). But as the scaffolds with folded strut structure were coated with TiO$_2$ slurry, the number and size of flaws was efficiently reduced as the slurry was deposited in the large voids and folds present on the strut surface (FIG. 3). This enhancement in the microstructural uniformity of the strut structure is considered to cause the observed dramatic improvement in compressive strength of the prepared TiO$_2$ foams (FIG. 5a).

Previous studies have shown that multiple coatings can lead to further improvement in the strength of reticulated ceramic foams. However, this improvement is usually achieved at the expense of porosity and interconnectivity of the pore network, which may ultimately restrict the use of such foams in their intended applications. In contrast, by the use of the recoating method presented herein, the number of the remaining defects in the ceramic struts was reduced by recoating the double-coated TiO$_2$ foams with very low viscosity TiO$_2$ slurry under vacuum conditions in order to avoid the increase in the strut thickness. Such vacuum infiltration process was found to lead in drastic improvement in the mechanical integrity of the TiO$_2$ foams due to further improved strut strength of the more uniform ceramic structure (FIGS. 3 and 5a). Vogt et al. 2010 have previously described a vacuum infiltration process in which the hollow interior of the replicated foams struts is filled with ceramic slurry, thus resulting in an increase in the compressive strength of these ceramic foams. However, the hollow space inside the ceramic struts can be considered practically closed porosity and the infiltration of the ceramic slurry into this hollow space is likely to be limited even under vacuum, particularly in foams with smaller strut sizes with narrower triangular voids within the strut interior. In addition, the viscosity of the slurry used in the vacuum infiltration procedure ought to be kept low in order to reach majority of the tortuous pore space inside the ceramic strut network through the few accessible openings, such as fractured struts and narrow cracks at the strut edges.

Curiously, reversing the order of the two applied processes (DC and VI) caused no significant alterations in either the pore architectural characteristics of the prepared TiO$_2$ foams or their compressive strength. It appears that the low viscosity slurry used in the VI process is deposited mainly in the micropores and small voids of the struts, while the centrifugation process effectively removes the excess slurry from the foam structure, leaving only a very thin coating on the strut surface. Due to the low viscosity of the used TiO$_2$ slurry even at low shear stresses, the slurry can be force into the remaining small flaws in the strut structure with the aid of vacuum, while the thicker DC slurry is deposited in the larger folds of the struts. The negligible increase in strut size due to the vacuum infiltrated coating is likely to arise from blockage of some of the smallest pore windows and accumulation of TiO$_2$ slurry at the strut junctures, which also caused the slight drop in the interconnectivity of the foam structure at (FIG. 5b). This reduction in the interconnectivity of the pore network was more pronounced when the vacuum infiltrated scaffolds were double-coated with thicker slurry, indicating that DC+VI process results in less blocked pore openings than applying the same procedures in reversed order (VI+DC). Nonetheless, the additional vacuum infiltrated low viscosity coating appears to be an effective method for improving the structural uniformity of the TiO$_2$ foam structure, and thus significantly enhancing the mechanical strength of the TiO$_2$ scaffolds while still maintaining appropriate pore architectural features of the TiO$_2$ scaffold structure.

Since the low viscosity coating used in the VI process appears to only have a negligible effect on the scaffold structure, the pore architectural characteristics are mainly dependent on the higher viscosity double coating procedure. As the interconnectivity of the pore volume has been identified as one of the most important characteristics for a bone scaffold, the number of blocked pore windows should be minimized in the scaffold structure by optimization of the double coating procedure. Viscosity of the slurry used for double coating the scaffolds (DC) had a notable influence on the uniformity of the TiO$_2$ foam structure with both low (30 g) and high (45 g) solid contents causing blockage of the pore windows (FIG. 4), and thereby influencing the interconnectivity of the pore network (FIG. 5b). Since the poor infiltration of the more viscous slurry resulted in blocked pore openings mainly at the outer edges of the TiO$_2$ foam, the effect of this blockage was not manifested in the 3D interconnectivity analysis as the selected VOI (volume of interest) excluded the outermost region of the scaffold cylinder. However, the blockage of the outer pore windows is likely to significantly hinder the cell and tissue penetration towards the scaffold interior and is therefore particularly undesirable. Controlling the viscosity of the third slurry was therefore identified as one of the most important processing parameters governing the uniformity and interconnectivity of the pore network when the mechanical integrity of ceramic foams is improved with the recoating procedure.

The method disclosed in the present document for providing a recoated titanium dioxide scaffold thus provides a scaffold with improved mechanical strength while not negatively affecting the pore architecture and interconnectivity of the pore network.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

REFERENCES

Brezny R, Green D J, Dam C Q. Evaluation of strut strength in open-cell ceramics. J Am Ceram Soc 1989; 72:885-889.

Fostad G, Hafell B, Førde A, Dittmann R, Sabetrasekh R, Will J, Ellingsen J E, Lyngstadaas S P, Haugen H J. Loadable TiO$_2$ scaffolds—A correlation study between processing parameters, micro CT analysis and mechanical strength. J Eur Ceram Soc 2009; 29:2773-2781.

Maniatopoulos et al., in Cell Tissue Res 254, 317-330, 1988

Moore M J, Jabbari E, Ritman E L, Lu L, Currier B L, Windebank A J, Yaszemski M J. Quantitative analysis of interconnectivity of porous biodegradable scaffolds with micro-computed tomography. J Biomed Mater Res Part A 2004; 71A:258-267.

Tiainen H, Lyngstadaas S P, Ellingsen J E, Haugen H J. Ultra-porous titanium oxide scaffold with high compressive strength. J Mater Sci: Mater Med 2010; 21:2783-2792.

Vogt U F, Gorbar M, Dimopoulos-Eggenschwiler P, Broenstrup A, Wagner G, Colombo P. Improving the properties of ceramic foams by a vacuum infiltration process. J Eur Ceram Soc 2010; 30:3005-3011.

J Pascual-Cosp, A. J Ramirez del Valle, J Garcia-Fortea, P. J Sánchez-Soto, Laser cutting of high-vitrified ceramic materials: development of a method using a Nd:YAG laser to avoid catastrophic breakdown, Materials Letters, Volume 55, Issue 4, August 2002, Pages 274-280, ISSN 0167-577X, 10.1016/S0167-577X(02)00377-4. (http://www.sciencedirect.com/science/article/pii/S067577X02003774).

Schwartzwalder, K., and Somers, A. V., Method of Making a Porous Shape of Sintered Refractory Ceramic Articles. U.S. Pat. No. 3,090,094, 1963.

Larry S., Liebovitch, Tibor Toth, A fast algorithm to determine fractal dimensions by box counting, Physics Letters A, Volume 141, Issues 8-9, 20 Nov. 1989, Pages 386-390, ISSN 0375-9601, http://dx.doi.org/10.1016/0375-9601(89)90854-2. (http://www.sciencedirect.com/science/article/pii/0375960189908542)

The invention claimed is:

1. A method for producing a recoated titanium dioxide scaffold, said method comprising:
    a) applying a first slurry comprising titanium dioxide to a combustible porous structure;
    b) allowing the first slurry to solidify on said combustible porous structure;
    c) removing said combustible porous structure from the solidified titanium dioxide slurry by a first sintering at about 400-550° C. to produce a titanium dioxide scaffold structure;
    d) subjecting the titanium dioxide scaffold structure of step c) to a second sintering at a temperature of at least 1300° C. for at least 10 hours to provide a single-coated titanium dioxide scaffold that essentially lacks an inner strut volume;
    e) applying a second slurry comprising titanium dioxide to said single coated titanium dioxide scaffold by vacuum infiltration and thereafter optionally subjecting said single-coated titanium dioxide scaffold to centrifugation;
    f) allowing the second slurry of step e) to solidify on the single-coated titanium dioxide scaffold; and
    g) performing a third sintering at a temperature of at least 1100° C. to provide a recoated titanium dioxide scaffold;
    h) applying a third slurry comprising titanium dioxide to the recoated titanium dioxide scaffold, and subjecting the scaffold to centrifugation;
    i) allowing the third slurry to solidify on the scaffold; and
    j) performing a further sintering at a temperature of at least 1100° C.; wherein the viscosity of the third slurry is lower than the viscosity of the first slurry and higher than the viscosity of the second slurry.

2. The method of claim 1, wherein said further sintering of step i) is performed for at least 10 hours.

3. The method of claim 2, wherein said further sintering of step i) is performed for 20-50 hours.

4. The method according to claim 1, wherein said third sintering of step g) is performed for about 2-15 hours.

5. The method according to claim 4, wherein said third sintering of step g) is performed for 3 hours.

6. The method according to claim 1, wherein the concentration of titanium dioxide in said second slurry is 300-900 mg/ml.

7. The method according to claim 6, wherein the concentration of titanium dioxide in said second slurry is 400-800 mg/ml.

8. The method according to claim 1, wherein the concentration of titanium dioxide in said third slurry is about 1300-1700 mg/ml.

9. The method according to claim 8, wherein the concentration of titanium dioxide in said third slurry is 1500-1700 mg/ml.

10. The method according to claim 1, wherein said vacuum infiltration is performed at at least 0.1 mbar.

11. The method according to claim 10, wherein said vacuum infiltration is performed at 0.1-0.3 mbar.

12. A recoated titanium dioxide scaffold obtainable by the method of:
    a. applying a first slurry comprising titanium dioxide to a combustible porous structure;
    b. allowing the first slurry to solidify on said combustible porous structure;
    c. removing said combustible porous structure from the solidified titanium dioxide slurry by a first sintering at about 400-550° C. to produce a titanium dioxide scaffold structure;
    d. subjecting the titanium dioxide scaffold structure of step c) to a second sintering at a temperature of at least 1300° C. for at least 10 hours to provide a single-coated titanium dioxide scaffold that essentially lacks an inner strut volume;
    wherein said method further comprises a vacuum infiltration procedure, wherein said vacuum infiltration procedure comprises the steps of:
    e. applying a second slurry comprising titanium dioxide to said single coated titanium dioxide scaffold by vacuum infiltration and thereafter optionally subjecting said single-coated titanium dioxide scaffold to centrifugation;
    f. allowing the second slurry of step e) to solidify on the single-coated titanium dioxide scaffold; and
    g. performing a third sintering at a temperature of at least 1100° C. to provide a recoated titanium dioxide scaffold.

13. A medical prosthetic device comprising a recoated titanium dioxide scaffold according to claim 12.

14. A recoated titanium dioxide scaffold according to claim 12 for use as a medical prosthetic device.

15. A recoated titanium dioxide scaffold according to claim 12 for use for the regeneration, repair, substitution and/or restoration of tissue.

* * * * *